(12) United States Patent
Corndorf et al.

(10) Patent No.: US 10,105,187 B2
(45) Date of Patent: Oct. 23, 2018

(54) SYSTEMS, APPARATUS, METHODS AND COMPUTER-READABLE STORAGE MEDIA FACILITATING SURGICAL PROCEDURES UTILIZING AUGMENTED REALITY

(71) Applicant: Medtronic, Inc., Minneapolis, ME (US)

(72) Inventors: Eric D. Corndorf, Minneapolis, MN (US); Andrzej M. Malewicz, Minneapolis, MN (US)

(73) Assignee: Medtronic, Inc., Minneapolis, MN (US)

( * ) Notice: Subject to any disclaimer, the term of this patent is extended or adjusted under 35 U.S.C. 154(b) by 43 days.

(21) Appl. No.: 15/236,750

(22) Filed: Aug. 15, 2016

(65) Prior Publication Data

US 2017/0056115 A1 Mar. 2, 2017

Related U.S. Application Data

(60) Provisional application No. 62/210,806, filed on Aug. 27, 2015.

(51) Int. Cl.
 G06T 7/00 (2017.01)
 A61B 34/20 (2016.01)
 (Continued)

(52) U.S. Cl.
 CPC .... A61B 34/20 (2016.02); *A61B 2017/00243* (2013.01); *A61B 2034/107* (2016.02);
 (Continued)

(58) Field of Classification Search
 CPC ....... G06T 7/0012; G06T 7/246; G06T 7/248; G06T 7/70; G06T 7/74; A61B 34/20; A61B 2034/2046; A61B 2034/2055; A61B 2034/2065; A61B 2090/363; A61B 2090/364; A61B 2090/3983
 See application file for complete search history.

(56) References Cited

U.S. PATENT DOCUMENTS 7,176,936 B2 2/2007 Sauer et al. .................. 345/592
7,655,014 B2 2/2010 Ko et al. ...................... 606/129
(Continued)

OTHER PUBLICATIONS

"Tunneling Tool," 6996T Technical Manual, Medtronic, Inc., 2011, 12 pages.

(Continued)

*Primary Examiner* — Andrew W Johns

(57) ABSTRACT

Techniques facilitating augmented reality-assisted surgery are provided. In one example, a method is provided that includes receiving, by a first device including a processor, image data associated with an external portion of a tool located within a body of a patient, wherein the image data includes first information indicative of a first fiducial marker on the external portion of the tool. The method also includes determining one or more relative positions of an internal portion of the tool within the body relative to one or more anatomical structures of the body based on the image data and a defined configuration of the tool. The method also includes generating one or more representations of the tool within the body relative to the one or more anatomical structures based on the one or more relative positions and the defined configuration of the tool.

23 Claims, 18 Drawing Sheets

(51) Int. Cl.
    *A61B 90/00*     (2016.01)
    *A61B 17/00*     (2006.01)
    *A61B 34/10*     (2016.01)

(52) U.S. Cl.
    CPC ........... *A61B 2034/2048* (2016.02); *A61B 2034/2055* (2016.02); *A61B 2034/2065* (2016.02); *A61B 2090/0807* (2016.02); *A61B 2090/365* (2016.02); *A61B 2090/373* (2016.02); *A61B 2090/3937* (2016.02); *A61B 2090/3983* (2016.02)

(56) References Cited

U.S. PATENT DOCUMENTS

| | | | |
|---|---|---|---|
| 7,774,044 B2 | 8/2010 | Sauer et al. | 600/424 |
| 8,157,813 B2 | 4/2012 | Ko et al. | 606/129 |
| 8,718,793 B2 | 5/2014 | O'Connor | 607/119 |
| 8,801,729 B2 | 8/2014 | Ko et al. | 606/129 |
| 2002/0082498 A1 | 6/2002 | Wendt et al. | 600/411 |
| 2014/0022283 A1 | 1/2014 | Chan et al. | G09G 5/377 |
| 2014/0200592 A1 | 7/2014 | O'Connor | A61N 1/0587 |
| 2014/0324068 A1 | 10/2014 | Ko et al. | A61N 1/05 |
| 2014/0330208 A1 | 11/2014 | Christie et al. | A61N 1/05 |
| 2014/0330287 A1 | 11/2014 | Thompson-Nauman et al. | A61N 1/05 |
| 2014/0330327 A1 | 11/2014 | Thompson-Nauman et al. | A61N 1/3962 |
| 2015/0105793 A1 | 4/2015 | Cole | A61N 1/059 |
| 2015/0133951 A1 | 5/2015 | Seifert et al. | A61N 1/0504 |
| 2015/0133952 A1 | 5/2015 | Seifert et al. | A61N 1/0504 |
| 2015/0133953 A1 | 5/2015 | Seifert et al. | A61N 1/05 |
| 2017/0119474 A1* | 5/2017 | Kronman | A61B 34/20 |

OTHER PUBLICATIONS

"Subcutaneous, unipolar lead with defibrillation coil electrode," 6996SQ Technical Manual, Medtronic, Inc., 2012, 22 pages.

Tung, SK, et al., "Initial Experience of Minimal Invasive Extra Cardiac Placement of High Voltage Defibrillator Leads," http://www.pulsus.com/ccc2007/abs/0697.htm, Last accessed Jan. 9, 2015, 2 pages.

Guenther, M., et al., "Substernal lead implantation: a novel option to manage DFT failure in S-ICD patients," Clinical Research in Cardiology, 2014, 3 pages.

Cigna, E., et al., "A new technique for substernal colon transposition with a breast dissector: Report of 39 cases," Journal of Plastic, Reconstructive & Aesthetic Surgery, 2006, pp. 343-346, vol. 59, Elsevier Ltd.

Dyrda, L., "Bringing a spine start-up to fruition—New technology in spine navigation," Becker's Spine Review, Mar. 17, 2015, http://www.beckersspine.com/orthopedic-a-spine-device-a-implant-news/item/24751-bring, Last accessed Mar. 23, 2015, 5 pages.

* cited by examiner

SYSTEMS, APPARATUS, METHODS AND COMPUTER-READABLE STORAGE MEDIA FACILITATING SURGICAL PROCEDURES UTILIZING AUGMENTED REALITY

CROSS-REFERENCE TO RELATED APPLICATION

This application claims priority to U.S. Provisional Application Ser. No. 62/210,806, filed Aug. 27, 2015, and entitled, "SYSTEMS, APPARATUS, METHODS AND COMPUTER-READABLE STORAGE MEDIA FACILITATING SURGICAL PROCEDURES UTILIZING AUGMENTED REALITY," the entirety of which is incorporated herein by reference.

TECHNICAL FIELD

This disclosure relates generally to medical devices and, more particularly, to systems, apparatus, methods and computer-readable storage media facilitating surgical procedures utilizing augmented reality.

BACKGROUND

Contemporary healthcare relies heavily on implantable medical devices (IMDs) to assist patients in leading healthy lives. Implantation of such IMDs as well as exploratory procedures for diagnosis and/or treatment of medical ailments typically involve surgical procedures contacting internal areas of a body of a patient. If these procedures are performed incorrectly or with the improper tools, damage can occur to the heart, lungs and other internal organs of the body. Further, these internal areas can be difficult to see because anatomical structures may obstruct the view of the surgeon. However, making large incisions in the body of a patient to facilitate the view of the surgeon is often undesirable. Accordingly, there is a desire for approaches that facilitate surgical procedures utilizing augmented reality.

SUMMARY

The following presents a simplified summary of one or more of the embodiments in order to provide a basic understanding of one or more of the embodiments. This summary is not an extensive overview of the embodiments described herein. It is intended to neither identify key or critical elements of the embodiments nor delineate any scope of embodiments or the claims. Its sole purpose is to present some concepts of the embodiments in a simplified form as a prelude to the more detailed description that is presented later. It will also be appreciated that the detailed description may include additional or alternative embodiments beyond those described in the Summary section.

Embodiments described herein include systems, apparatus, methods and computer-readable storage media facilitating surgery using augmented reality. The term "surgery" as used herein refers to the treatment or evaluation of injuries, medical conditions or disorders of the body by incision or manipulation, especially with instruments. In some embodiments, the surgery is a substernal lead implantation procedure. However, many of the disclosed embodiments can be applied to other surgical procedures involving an instrument.

In one embodiment, a method is provided. The method can include receiving, by a first device including a processor, image data associated with an external portion of a tool located within a body of a patient, wherein the image data comprises first information indicative of a first fiducial marker on the external portion of the tool; and determining one or more relative positions of an internal portion of the tool within the body relative to one or more anatomical structures of the body based on the image data and a defined configuration of the tool. The method can also include generating one or more representations of the tool within the body relative to the one or more anatomical structures based on the one or more relative positions and the defined configuration of the tool.

In some embodiments, the image data also includes second information indicative of an external part of the body, and the determining the one or more relative positions of the internal portion of the tool can include determining one or more positions of the first fiducial marker relative to the external part of the body. The image data can also include second information indicative of a second fiducial marker located on an external part of the body, and the determining the one or more relative positions of the internal portion of the tool can include determining one or more positions of the first fiducial marker relative to the second fiducial marker.

In some embodiments, the patient is a human and the second fiducial marker is located on an external area of the body over and adjacent to a sternum of the patient. By way of example, but not limitation, the tool can be inserted into the body via an incision in the body and the second fiducial marker can be located proximate to the incision.

In some embodiments, the tool includes an elongated shaft having a plurality of markers and the image data includes one or more visible subsets of the plurality of markers. Determining the one or more relative positions of the internal portion of the tool within the body can be based on determining the one or more visible subsets of the plurality of markers relative to the plurality of markers. In some embodiments, determining the one or more relative positions of the internal portion of the tool within the body includes determining an orientation of the internal portion of the tool within the body.

In some embodiments, the method also includes displaying, by the first device, the one or more representations on a first display of the first device, wherein the one or more representations facilitate guidance of the tool to a target location within the body. In some embodiments, a second device performs the display of the one or more representations.

In another embodiment, a medical device is provided. The medical device can include an elongated shaft comprising a distal end and a proximal end, wherein the distal end is configured for insertion into a body of a patient; a handle coupled to the proximal end of the elongated shaft; one or more fiducial markers located on the elongated shaft; and an orientation unit including an accelerometer configured to collect orientation information regarding an orientation of the medical device and provide the orientation information to another device, wherein an orientation and position of the medical device relative to the body of the patient are determined based on the orientation information and image data captured by one of the one or more fiducial markers.

The one or more fiducial markers can be configured to facilitate optical tracking of one or more positions of an internal portion of the elongated shaft inside the body of the patient. In some embodiments, one or more fiducial markers are located on an outer surface of the elongated shaft. In some embodiments, one or more fiducial markers are positioned to be detected by a single stationary camera irrespective of an orientation of the medical device relative to the body of the patient.

In yet another embodiment, a tangible computer-readable storage medium is provided. The computer-readable storage medium can include computer-readable instructions that, in response to execution, cause a device to perform operations. The operations can include: receiving image data associated with an external portion of a medical device inserted within a body of a patient, wherein the image data comprises first information associated with a first fiducial marker on the external portion of the medical device; and determining a relative position of an internal portion of the medical device within the body relative to one or more anatomical structures of the body based on the image data and a configuration of the medical device. In some embodiments, the operations can include generating a representation of the internal portion of the medical device within the body relative to the one or more anatomical structures based on the relative position and the configuration of the medical device.

Other embodiments and various non-limiting examples, scenarios and implementations are described in more detail below. The following description and the drawings set forth certain illustrative embodiments of the specification. These embodiments are indicative, however, of but a few of the various ways in which the principles of the specification may be employed. Other advantages and novel features of the embodiments described will become apparent from the following detailed description of the specification when considered in conjunction with the drawings.

DETAILED DESCRIPTION

The following detailed description is merely illustrative and is not intended to limit embodiments and/or application or uses of embodiments. Furthermore, there is no intention to be bound by any expressed or implied information presented in the preceding Technical Field, Background or Summary sections, or in the Detailed Description section.

One or more embodiments are now described with reference to the drawings, wherein like referenced numerals are used to refer to like elements throughout. In the following description, for purposes of explanation, numerous specific details are set forth in order to provide a more thorough understanding of the one or more embodiments. It is evident, however, in various cases, that the one or more embodiments can be practiced without these specific details.

Additionally, the following description refers to components being "connected" and/or "coupled" to one another. As used herein, unless expressly stated otherwise, the terms "connected" and/or "coupled" mean that one component is directly or indirectly connected to another component, mechanically, electrically, wirelessly, inductively or otherwise. Thus, although the figures may depict example arrangements of components, additional and/or intervening components may be present in one or more embodiments.

Figure 1:
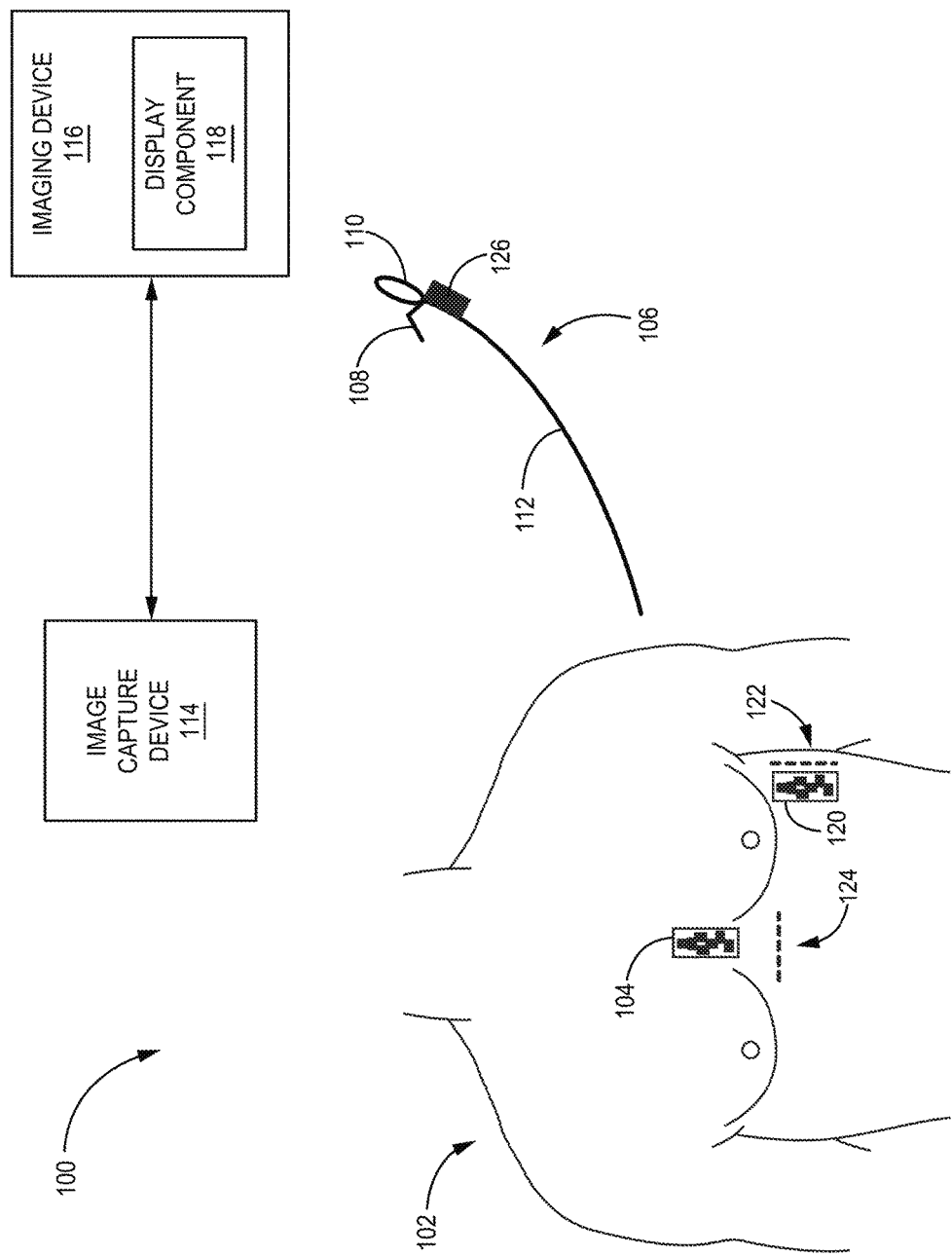
FIG. 1 illustrates a schematic diagram of an example, non-limiting system facilitating surgery using augmented reality in accordance with one or more embodiments described herein.

With reference now to the drawings, FIG. 1 illustrates a schematic diagram of an exemplary, non-limiting system facilitating surgery using augmented reality in accordance with one or more embodiments described herein. Aspects of systems, apparatuses and/or processes explained in this disclosure can include machine-executable components embodied within machine(s), e.g., embodied in one or more computer readable mediums (or media) associated with one or more machines. Such components, when executed by the one or more machines, e.g., computer(s), computing device(s), virtual machine(s), etc., can cause the machine(s) to perform the operations described.

In the embodiment shown, system 100 includes a patient 102, a surgical instrument 106, an image capture device 114 and an imaging device 116. In various embodiments, one or more of the surgical instrument 106, image capture device 114 and/or imaging device 116 can be electrically and/or communicatively coupled to one another to perform one or more functions of system 100.

System 100 incorporates augmented reality technology with surgical apparatus and/or procedures (involving instrument 106) to provide visual image guidance in association with employing and/or navigating the instrument 106 inside a body 102 of the patient. In an embodiment, system 100 can enable real-time tracking and/or visualization of the portion of the instrument 106 that is obstructed from external view of the operator of the instrument 106. For example, a portion of the instrument 106 can be obstructed from view due to insertion into an area of the body 102 that is not visible to the operator of the instrument 106 (e.g., surgeon or otherwise) or that is partially occluded by tissue, body fluids or the like as the instrument 106 is being used to perform surgery. In particular, the position and/or orientation of the instrument 106 inside the body 102 relative to various internal and/or external anatomical structures of the body 102 can be determined as the instrument 106 is being maneuvered inside the patient (e.g., in-vivo). In some embodiments, the position and/or orientation of the instrument 106 can be determined in real-time (e.g., within a few seconds or milliseconds after positioning the instrument or after a change in positioning of the instrument 106).

Electronic information indicative of two-dimensional (2-D) and/or three dimensional (3-D) representations of the instrument 106 inside the body 102 can be generated and/or displayed. In some embodiments, the representations can be integrated within a display showing a 2-D or 3-D visual model of the body 102 and the internal and/or external anatomical structures of the body 102.

For example, a 2-D and/or 3-D model of internal and/or external anatomical structures of the patient can be generated (by system 100 or another system) based on previously captured image data of the patient and/or known anatomical structures of the human body. The previously captured image data of the body 102 of the patient can include image data captured using various medical imaging technologies such as but not limited to: X-ray radiography, magnetic resonance imaging, medical ultrasonography or ultrasound, endoscopy, elastography, tactile imaging, thermography, medical photography (e.g., X-ray computed tomography (X-ray CT) or computerized axial tomography scan (CAT scan)) and/or nuclear medicine functional imaging techniques such as positron emission tomography.

In various embodiments, the visual model generated by system 100 can vary in complexity based on the area of the body 102 in which the instrument 106 is being used and/or the type of surgical operation being performed. For example, the visual model can include various internal and/or external anatomical structures of the body 102. The internal and/or external anatomical structures can include, but are not limited to, bones, muscles, organs, tissues, glands, ligaments, tendons, nerves, veins, and vessels. Foreign structures located inside the body 102, such as IMDs, can also be included in the model in some embodiments.

In accordance with various embodiments of system 100, as an instrument (e.g., instrument 106) is located within, inserted into and/or maneuvered within the body 102 of the patient, 2-D and/or 3-D representations of the in-vivo portion of the instrument 106 can be generated. In some embodiments, the 2-D and/or 3-D representations of the in-vivo portion of the instrument 106 can be integrated within a visual model of the body 102 at the actual position of the instrument 106 and/or orientation relative to the modeled anatomical structures. This visualization of the instrument 106 as the instrument 106 appears inside the body 102 can be displayed for view by an operator of the instrument 106 (e.g., surgeon) via a display device, as a holographic projection or any other approaches for displaying information. Accordingly, the surgeon can view the instrument 106 inside the body 102 relative to anatomical landmarks without the need to expose the instrument 106 and/or anatomical landmarks (e.g., via further cutting or opening of the body 102). In some embodiments, the displayed information can be provided in real-time (e.g., within 1-3 seconds after the information is gathered in-vivo). As used in this disclosure, the term "user" can refer to a person, entity, device, or system, or a combination of a person, entity, device, or system. For example, in some embodiments, a user can include a robot having a robotic arm fully controlled or controlled in part by a computing device or by a surgeon to hold and/or maneuver the instrument 106 during surgery. In some embodiments, the user is a surgeon.

In accordance with various embodiments, system 100 is configured to employ optical tracking to enable visualization of a portion of instrument 106 that is in-vivo relative to one or more internal and/or external anatomical structures of the body 102. According to these embodiments, an image capture device 114 is positioned outside the body 102 of the patient and captures image data of the portion of the instrument 106 that is located ex-vivo when the instrument 106 is located within, inserted into and/or maneuvered within the body 102 of the patient.

The image data can also include information indicative of one or more other external features and/or structures included in the operating environment, such as an external portion of the body 102 of the patient, a portion of the operating table upon which the body 102 of the patient is rested, a fiducial marker that has been placed on the body 102 of the patient (e.g., sternal fiducial marker 104 and/or incision fiducial marker 120) or the like. As used herein, the term "external" means outside of the body, or ex-vivo. One or more of the external features and/or structures can serve as one or more reference points to facilitate determining a spatial relationship between the instrument 106, the reference points, actual anatomical structure of the body 102, and/or visually modeled structures of the body 102, as the instrument 106 is located inside the body 102.

In some embodiments, the captured image data can be provided to an imaging device 116. For example, the captured image data can be transmitted via wireless or wired link from the image capture device 114 to the imaging device 116. The imaging device 116 can be configured to process the image data and determine a position and/or orientation of one or more portions of the instrument 106. For example, in some embodiments, the imaging device 116 can be configured to process the image data and determine a position and/or orientation of the in-vivo portion of the instrument 106 relative to the one or more internal and/or external anatomical structures of the body 102.

In some embodiments, the imaging device 116 can generate 2-D and/or 3-D representations of the in-vivo portion (and/or the ex-vivo portion) of the instrument 106. In some embodiments, the imaging device 116 can integrate the 2-D and/or 3-D representations of the instrument 106 within a previously generated 2-D and/or 3-D model of the internal and/or external structures of the body 102 at the determined position and/or orientation of the portion of the instrument 106 relative to the modeled anatomical structures.

In some embodiments, the imaging device 116 can determine the position and/or orientation of the in-vivo portion of the instrument 106 relative to the one or more anatomical structures based on the captured image data associated with the ex-vivo portion of the instrument 106, as well as a known configuration (e.g., size and/or shape) of the instrument 106, a known position of a captured reference point relative to a 2-D or 3-D coordinate space, and/or known positions of the one or more anatomical structures relative to the 2-D or 3-D coordinate space. In one example, the imaging device 116 can compare the size and/or shape (as determined via the image data) of the ex-vivo portion of the instrument 106 to a known model (size and shape) of the entire instrument 106. The portion of the known model of the instrument 106 that is not included in the captured ex-vivo portion can be determined by the imaging device 116 to correspond to the in-vivo portion of the instrument 106. The imaging device 116 can then generate a representation of the in-vivo portion and combine the representation of the in-vivo portion with the real image data or a model of the ex-vivo portion.

In some embodiments, the imaging device 116 can determine the position and/or orientation of the in-vivo portion of the instrument 106 relative to the one or more anatomical structures of the body 102 based on a determined position and/or orientation of the ex-vivo portion of the instrument 106 relative to a defined reference point or object. According to this embodiment, the actual positions and orientations of the one or more internal and/or external anatomical structures of the patient relative to a 2-D or 3-D coordinate space can be determined. For example, the 2-D or 3-D model of the internal and/or external anatomical structures of the body 102 can be aligned or correlated to an actual position and/or orientation of the body 102 of the patient relative to a 2-D or 3-D coordinate space. A relative position of an actual reference point or object in the 2-D or 3-D coordinate space can also be known or defined. The imaging device 116 can thus determine a position and/or orientation of the ex-vivo portion of the instrument 106 in the coordinate space relative to the one or more reference points and employ triangulation to determine the position and/or orientation of the ex-vivo portion of the instrument 106 relative to the modeled anatomical structures.

In some implementations, the imaging device 116 can determine the position and/or orientation of the in-vivo portion of the instrument 106 relative to the modeled anatomical structures based on the position and/or orientation of the ex-vivo portion relative to the modeled anatomical structures and a known or defined geometry of the instrument 106.

In some embodiments, the captured image data can include depth information for the instrument 106. The depth information can correspond to a distance between the image capture device 114 and features (e.g., pixels) included in the captured image data (e.g., points along the ex vivo portion of the tool, points on the reference object, points on the body 102 of the patient, etc.). The imaging device 116 can employ this depth data to determine the relative positions and/or orientations of the ex-vivo portion of the instrument 106 relative to a 3-D coordinate space and a reference point included in the captured image data for which the position relative to the 3-D coordinate space is known. The imaging device 116 can then determine the position and/or orientation of the in-vivo portion of the instrument 106 relative to the 3-D coordinate space based on the determined position and/or orientation of the ex-vivo portion relative to the 3-D coordinate space.

In addition to or as an alternative to the optical tracking and/or visualization/display techniques discussed herein, in some embodiments, system 100 can perform optical tracking of the ex-vivo portion of the instrument 106 using visible fiducial markers on the instrument 106. For example, in various exemplary embodiments, the instrument 106 can include one or more fiducial markers. In some embodiments, the one or more fiducial markers (not shown) can include a pattern that is defined and/or known by the imaging device 116.

At least one fiducial marker can be provided at a location on the instrument 106 adapted or intended to remain outside of the body 102 when the instrument 106 is inserted inside the body 102. As such, the fiducial marker is capable of being captured by the image capture device 114. For example, the instrument 106 can include a handle 110 and a platform 108 near the handle 110 that is configured to remain outside of the body 102 of the patient during use of the instrument 106. According to this example, a fiducial marker can be located on the platform 108. Fiducial marker 200 will be shown and described with reference to FIG. 2, for example.

With reference to FIG. 1, according to one or more of these embodiments, the image capture device 114 can be configured to capture image data of the ex-vivo portion of the instrument 106, including the fiducial marker(s) on the ex-vivo portion of the instrument 106. The image capture device 114 can be also configured to capture image data of at least one reference point or object near or within a defined distance of the instrument 106 (e.g., within the visual capture space of the image capture device 114) having a known position relative to a 2-D or 3-D coordinate space. In some embodiments discussed, the reference point or object can include a second fiducial marker placed on the body 102 of the patient (e.g., sternal fiducial marker 104 and/or incision fiducial marker 120). With reference to FIG. 1, the imaging device 116 can receive and/or analyze the image data to determine a position and/or orientation of the instrument 106 relative to a modeled representation of the internal and/or external anatomical structures of the body 102 of the patient that has been correlated to the 2-D or 3-D coordinate space. In various embodiments, the imaging device 116 can receive and/or analyze the image data to determine a position and/or orientation of the instrument 106 relative to a modeled representation of the internal and/or external anatomical structures of the body 102 of the patient that has been correlated to the 2-D or 3-D coordinate space notwithstanding a portion of the instrument 106 is located in-vivo.

In some embodiments, the imaging device 116 determines the size and/or shape of the entire instrument 106, or receives previously determined information that defines the size and/or shape of the entire instrument 106 or one or more substantial portions of the instrument 106. For example, in various embodiments, the imaging device 116 can determine the size and/or shape of 75%, 95% or 100% of the entirety of the instruments.

In some embodiments, the imaging device 116 can determine or receive previously determined data that defines, or that can be employed to define, the three-dimensional geometry of the instrument 106. Data regarding the structure and/or geometry of the instrument 106 can also identify a position of at least one fiducial marker of the instrument 106 relative the structure and/or geometry of the instrument 106. According to this embodiment, the imaging device 116 can be configured to recognize the unique pattern of the fiducial marker in the captured image data and determine a position and orientation of the fiducial marker in the 2-D or 3-D coordinate space by mapping the position and orientation of the fiducial marker to the known position of one or more reference points in the 2-D or 3-D coordinate space. Using the known relationship between the fiducial marker and the 2-D and/or 3-D geometry of the instrument 106, the imaging device 116 can further determine the position and orientation of the in-vivo and ex-vivo portions of the instrument 106 relative to the 2-D and/or 3-D coordinate space. In some embodiments, the imaging device 116 can employ depth information included in the image data that identifies a distance from the image capture device to the fiducial marker and/or the reference point to facilitate calculating the current position and/or orientation of the fiducial marker.

In some implementations, when the image capture device 114 is provided at a fixed position throughout the surgical procedure, a vantage point of the image capture device relative to an appearance of the fiducial marker in the captured image data can also be used to determine an orientation of the instrument 106. For example, the imaging device 116 can determine or be provided with information that correlates various rotational positions of the instrument 106 in a 3-D coordinate space with specific appearances of the fiducial marker and/or a visible and distinguishing portion of a pattern of the fiducial marker.

Once the position and/or orientation of the instrument 106 (or the ex-vivo portion of the instrument 106) relative to the 2-D and/or 3-D coordinates space is determined, the position and/or orientation of the in-vivo portion of the tool can be mapped to a model of the anatomical structures of the patient when the model is correlated to the same 2-D and/or 3-D space using the techniques discussed above. For example, the imaging device 116 can determine an actual position and/or orientation of the body 102 of the patient relative to the 2-D and/or 3-D coordinate space. Imaging device 116 can further superimpose a known model of the anatomical features of the body 102 of the patient on the same 2-D and/or 3-D coordinate space.

In some embodiments, after the location and/or orientation of the ex-vivo portion of the instrument 106 relative to the 2-D and/or 3-D coordinate space is determined, the position and/or orientation of the in-vivo portion relative to the 2-D and/or 3-D coordinate space is determined based on a known configuration (e.g., size and/or shape) of the instrument 106. The imaging device 116 can integrate a 2-D and/or 3-D representation of the instrument 106 into the 2-D and/or 3-D anatomical visual model at the determined position and/or orientation of the instrument 106.

Figure 2:
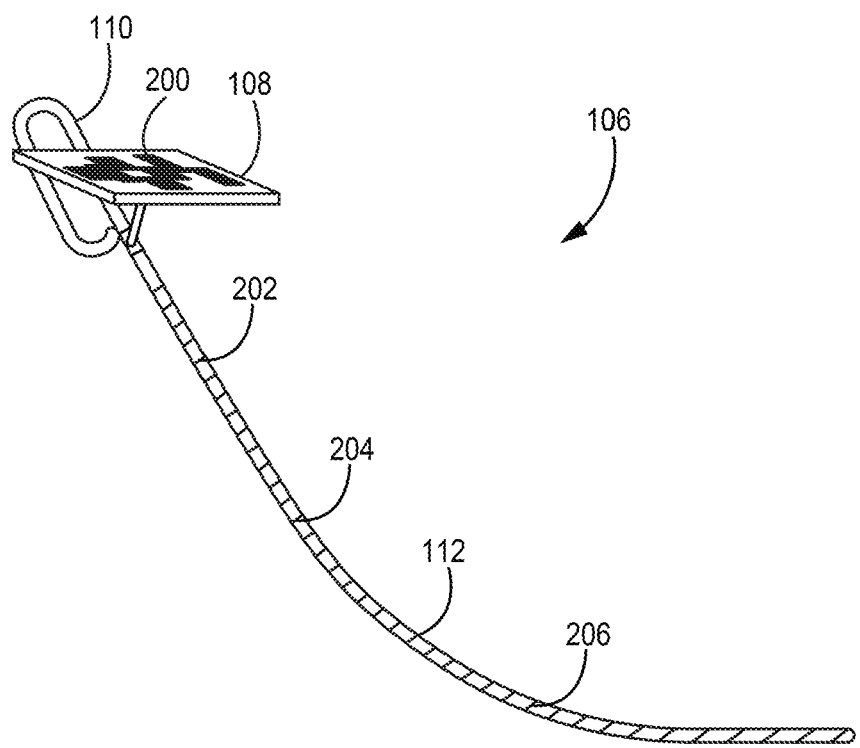
FIG. 2 illustrates a schematic diagram of an example, non-limiting instrument that facilitates surgery using augmented reality in accordance with one or more embodiments described herein.

FIG. 2 illustrates a schematic diagram of an example, non-limiting instrument 106 that facilitates surgery using augmented reality in accordance with one or more embodiments described herein. With reference to FIGS. 1 and 2, in another embodiment, the instrument 106 can also include a plurality of markers (shown as markers 202, 204, 206 of FIG. 2) along one or more portions of an elongated shaft 112 of the instrument 106. For example, instrument 106 can include an elongated shaft 112 that is configured to be inserted into the body 102 at various depths. The elongated shaft 112 can have a plurality of known markers 202, 204, 206 or gradations on the length of the elongated shaft 112 (e.g., akin to gradations of a ruler).

The relative positions of the markers with respect to a distal end of the instrument 106 (e.g., the end of the instrument 106 to be inserted into the body 102) and a proximal end of the instrument 106 (e.g., the end of the instrument 106 having the handle 110) can be known in some embodiments. According to these embodiments, the image capture device 114 can capture image data of the ex-vivo portion of the instrument 106. The imaging device 116 can analyze the image data to identify a subset of the plurality of markers 202, 204, 206 that are present and/or detectable in the image data. In some embodiments, using a subtraction technique, the image capture device 114 can determine another subset of the plurality of the markers 202, 204, 206 that are located in-vivo. Using a known relationship between the configuration of the instrument 106 and the locations of the plurality of markers 202, 204, 206 on the instrument 106 relative to the distal and proximal ends of the instrument 106, the imaging device 116 can determine the portion or length of the instrument 106 that is located in-vivo.

In various embodiments, as described herein, instrument 106 can be, correspond to or be coupled to a tunneling tool employed to generate a route for implantation of one or more IMDs. In one embodiment, the IMD can be or include a lead of an extravascular implantable cardioverter defibrillator (ICD) system having electrodes placed underneath/below the sternum/ribcage.

With reference to FIG. 2, as shown, the elongated shaft 112 can have a curved geometry in some embodiments. In other embodiments, any number of other suitable geometries of the elongated shaft 112 can be employed.

In some embodiments, the geometry and/or length of the elongated shaft 112 can be adjusted by a user of the instrument 106 prior to implantation into the body 102 to suit a particular anatomy of the patient. For example, the shaft 112 can be configured to be shaped into a plurality of different configurations having predefined geometries. According to this example, the imaging device 116 can detect and determine the particular configuration and associated geometry of the instrument 106 prior to insertion based on image data captured of the instrument 106 by image capture device 114, and/or a user of the instrument 106 can provide input to the imaging device 116 identifying the particular configuration of the instrument 106. The elongated shaft 112 can include a plurality of markers 202, 204, 206. While three markers 202, 204, 206 are indicated, in various embodiments, the markers on the elongated shaft 112 can be any number and are generally indicated by striped pattern on the elongated shaft 112 shown in FIG. 2.

In some embodiments, the distances between the respective markers and the distal and proximal ends of the instrument 106 and/or the distances between each of the markers can be predetermined and/or known. These markers (e.g., markers 202, 204, 206) can facilitate determining the length of a portion of the instrument 106 that is located in-vivo during use. The instrument 106 further includes a fiducial marker 200 located on a platform 108 that extends from a portion of the elongated shaft 112.

Figure 3:
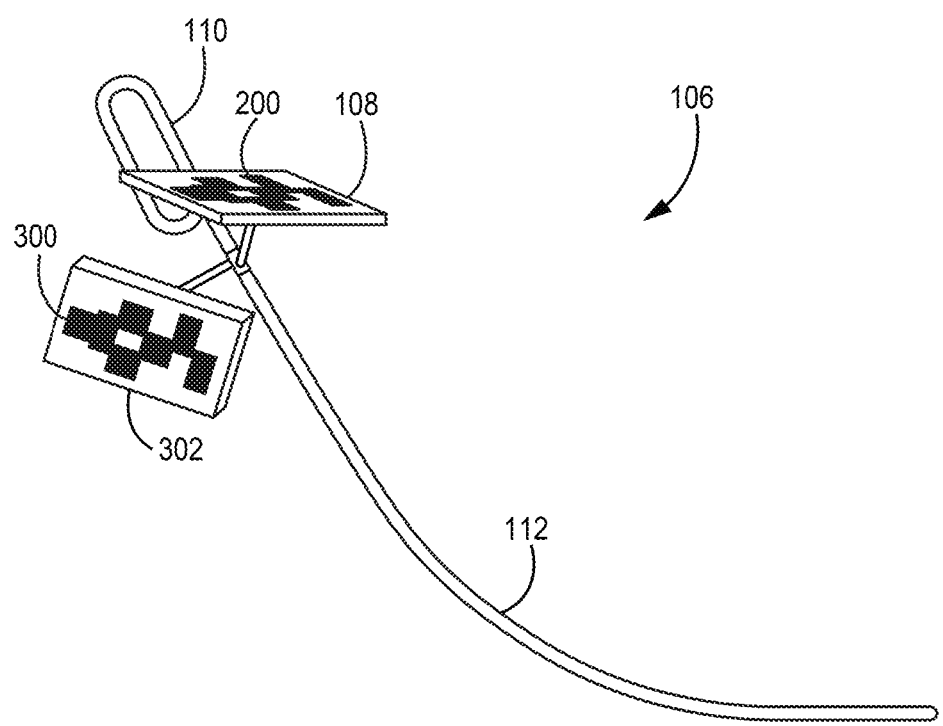
FIG. 3 illustrates a schematic diagram of an example, non-limiting instrument that facilitates surgery using augmented reality in accordance with one or more embodiments described herein.

FIG. 3 illustrates a schematic diagram of another example, non-limiting instrument 106 that facilitates surgery using augmented reality in accordance with one or more embodiments described herein. As shown in FIG. 3, in addition to the fiducial marker 200 located on platform 108, the instrument 106 includes another fiducial marker 300 on another platform 302. Repetitive description of like elements employed in respective embodiments disclosed herein is omitted for sake of brevity.

In some embodiments, as shown, platform 302 can have a different position and orientation relative to the elongated shaft 112 of the instrument 106. In accordance with this embodiment, the fiducial markers 200, 300 located on the respective platforms 108, 302 are different from one another. By including two or more different fiducial markers at different positions and/or orientations relative to the elongated shaft 112, the position and orientation of the instrument 106 relative to a 2-D or 3-D coordinate space can be more accurately determined as the instrument 106 is moved and/or rotated.

Figure 4:
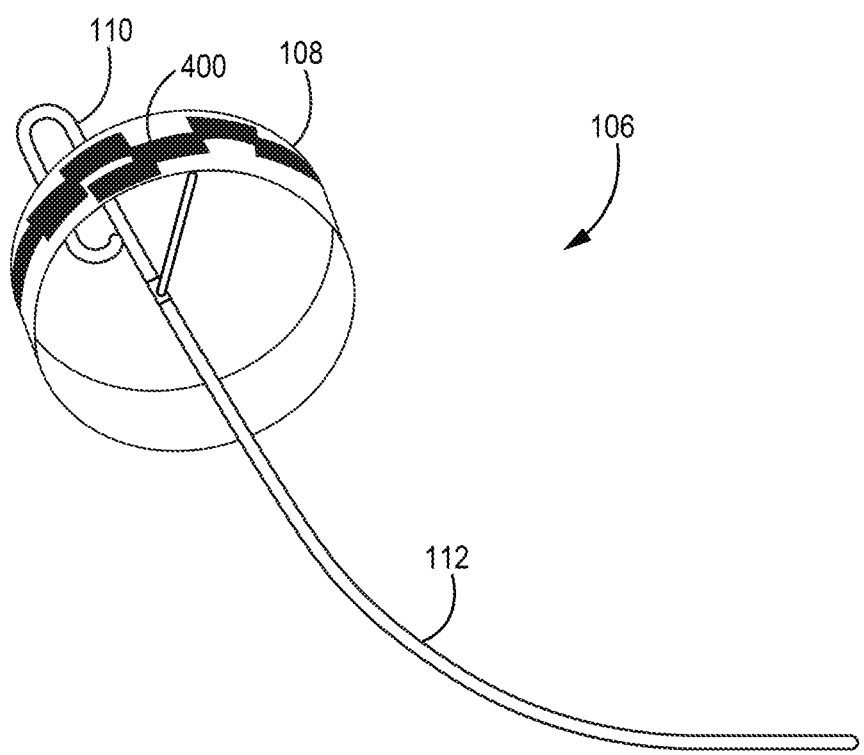
FIG. 4 illustrates a schematic diagram of an example, non-limiting instrument that facilitates surgery using augmented reality in accordance with one or more embodiments described herein.

FIG. 4 illustrates a schematic diagram of an example, non-limiting instrument 106 that facilitates surgery using augmented reality in accordance with one or more embodiments described herein. As shown in FIG. 4, platform 108 has a cylindrical ring configuration formed around a proximal end of the instrument 106. Repetitive description of like elements employed in respective embodiments disclosed herein is omitted for sake of brevity.

The platform 108 includes a fiducial marker 400 disposed on the platform 108 and/or provided around the entire circumference of the outer wall of the ring. In accordance with this embodiment, the pattern of the fiducial marker 400 can be non-repetitive and/or non-uniform such that different radial areas of the outer wall have different patterns. With this embodiment, the orientation of the instrument 106 can be more accurately detected based on the radial portion of the fiducial marker 400 on the ring that is included in a captured image. In some embodiments, although not depicted, the inner wall of the ring can also include a unique and/or non-uniform fiducial pattern around the circumference of the inner wall to further facilitate determining a position and/or orientation of the instrument 106 relative to a 3-D coordinate space.

Referring back to FIG. 1, in some embodiments, instrument 106 can include an orientation unit 126 that further facilitates accurately determining an orientation of the instrument 106 relative to a 2-D or 3-D coordinate space after the instrument 106 is inserted into and/or maneuvered in the body 102 of the patient. The orientation unit 126 can be configured to capture orientation data as the instrument 106 is moved and/or rotated. In some embodiments, the orientation unit 126 can include a processor that is configured to process the orientation data to determine an orientation of the instrument 106. In some embodiments, the orientation unit 126 can provide the orientation data to the imaging device 116 for processing. In some embodiments, the orientation unit 126 can transmit the orientation data to the imaging device 116 via wireless and/or wired channel.

In some implementations, the orientation unit 126 includes an accelerometer and circuitry, hardware, software, or a combination of hardware and software, associated with the operation of the accelerometer. In some embodiments, the orientation unit 126 can also include a power source and/or a transmitter capable of wirelessly transmitting captured or processed orientation data to the imaging device 116. In another embodiment, the imaging device 116 and the instrument 106 can be communicatively and electrically coupled via a cable (not shown).

In one or more embodiments, the imaging device 116 can employ the accelerometer data to determine an accurate orientation of the instrument 106 relative to a 2-D and/or 3-D coordinate space and a reference point (or points) included in the actual operating environment. The imaging device 116 can also combine the accelerometer orientation data with positional data for the instrument 106 determined based on captured image data (via the image capture device 114). The imaging device 116 can also compare an orientation calculation for the instrument 106 determined based on data obtained from the orientation unit 126 with another orientation calculation determined by the imaging device 116 based on captured image data (in accordance with the manners described above) to calibrate additional orientation determinations based on captured image data.

Image capture device 114 can include various types of 2-D and 3-D imaging devices or cameras capable of capturing digital still images and/or video. The resolution of the digital still images and/or video captured by the image capture device 114 can vary in different embodiments. In an embodiment, the image capture device 114 includes a camera capable of capturing depth data (e.g., a 3-D camera) for respective pixels in a captured digital image. Examples of 3-D capture devices include, but are not limited to, light detection and ranging cameras (LIDARs), hand-held laser line scanners, structured light projectors paired with cameras such as the Microsoft® Kinect, other structured light systems, stereo cameras with software for depth derivation, stereo cameras paired with pattern projection systems as well as software for depth derivation, time-of-flight cameras, video cameras capable of structure-from-motion calculations, and/or lightfield cameras.

In some embodiments, a plurality of image capture devices can be combined or a 3-D image capture device can be paired with a 2-D color camera to provide color detail for the captured 3-D information. For example, one or more image capture devices (e.g., image capture device 114) can be located at various positions and/or orientations relative to the operating area of the patient 102 such that the respective image capture devices can capture different perspectives of the body 102 of the patient, the instrument 106, and various other reference points or landmarks. Image data from the respective cameras can also be combined to determine a highly accurate position and/or orientation of the instrument 106 relative to a 3-D coordinate space.

In one or more embodiments, the image capture device 114 is configured to remain in a fixed position relative to the body 102 of the patient. The location of the image capture device 114 can vary depending on the area of the body 102 of the patient upon which surgery is being performed. For example, the image capture device 114 can be positioned such that the operating area on the patient is substantially or directly below and/or perpendicular to the image capture device 114. In another example, the image capture device 114 can be positioned on a side of the body 102 of the patient such that the image capture device 114 is substantially coplanar with the operating area. Still in other examples, the position of the image capture device 114 can be above and/or around the operating area of the patient at various pitches relative to the operating area. In other embodiments, the image capture device 114 can move to different positions and/or orientations relative to the body 102 of the patient during an augmented reality surgical procedure.

Still in yet another embodiment, the image capture device 114 can be worn by a user, such as a surgeon performing the surgery and employing the instrument 106. For example, the image capture device 114 can be included in a head mount that is worn by the surgeon such that the field of view of the image capture device 114 corresponds to the field of view of the surgeon. In another example, the image capture device 114 can be located in a pair of goggles or glasses worn by the surgeon.

A described herein, with system 100, one or more visualizations including a 2-D or 3-D representation of a tracked instrument 106 in-vivo relative to one or more 2-D or 3-D internal and/or external anatomical structures of the body 102 can be presented to a user via a device display or as a 3-D hologram. In the embodiment depicted in system 100, the imaging device 116 includes a display component 118 to facilitate rendering these visualizations. The display component 118 can include hardware, software, or a combination of hardware and software, that facilitates generating a graphical interface that includes the patient 2-D or 3-D representations and/or that facilitates generating a 3-D hologram of the patient 2-D or 3-D representations. For example, display component 118 can include a display screen of the imaging device 116. The location of the display screen can vary depending on the location, size, features, and functionality of the imaging device 116. For example, the imaging device 116 and the display screen of the imaging device 116 can be positioned in a suitable location in the operating room remote from the surgeon and the body 102 of the patient and/or at a location that can be viewed by the surgeon during surgery.

In another example, the imaging device 116 can include a wearable computing device, such as a computing device that is located in a head mount display or a pair of glasses or goggles. According to this example, the display screen can be positioned near the field of view of the surgeon, such as on the lenses, on a portion of a lens of the glasses or goggles, or as an extension of the head mount display.

Still in yet another embodiment, the imaging device 116 can include a wearable glasses computing device or a goggles-based computing device with a display component 118 configured to generate 3-D representations of objects and/or integrate the 3-D representations onto the lenses of the glasses such that the 3-D representations are displayed spatially integrated into the real world environment that is being seen be the user through the glasses. For example, as the user looks through the glasses at the chest of the patient, the user can see an augmented reality representation of at least a portion of the chest of the patient that includes internal anatomical structures of the chest. In essence, when looking through such an imaging device, the user can see a 3-D visualization of the chest as though the external structure (e.g., skin) of the chest has been cut open and removed to reveal the internal structures. According to this embodiment, the 3-D visualization of the anatomical structures can also include a 3-D representation of the in-vivo portion of the instrument 106 at the determined position and/or orientation of the instrument 106 relative to the anatomical structures.

Figure 5:
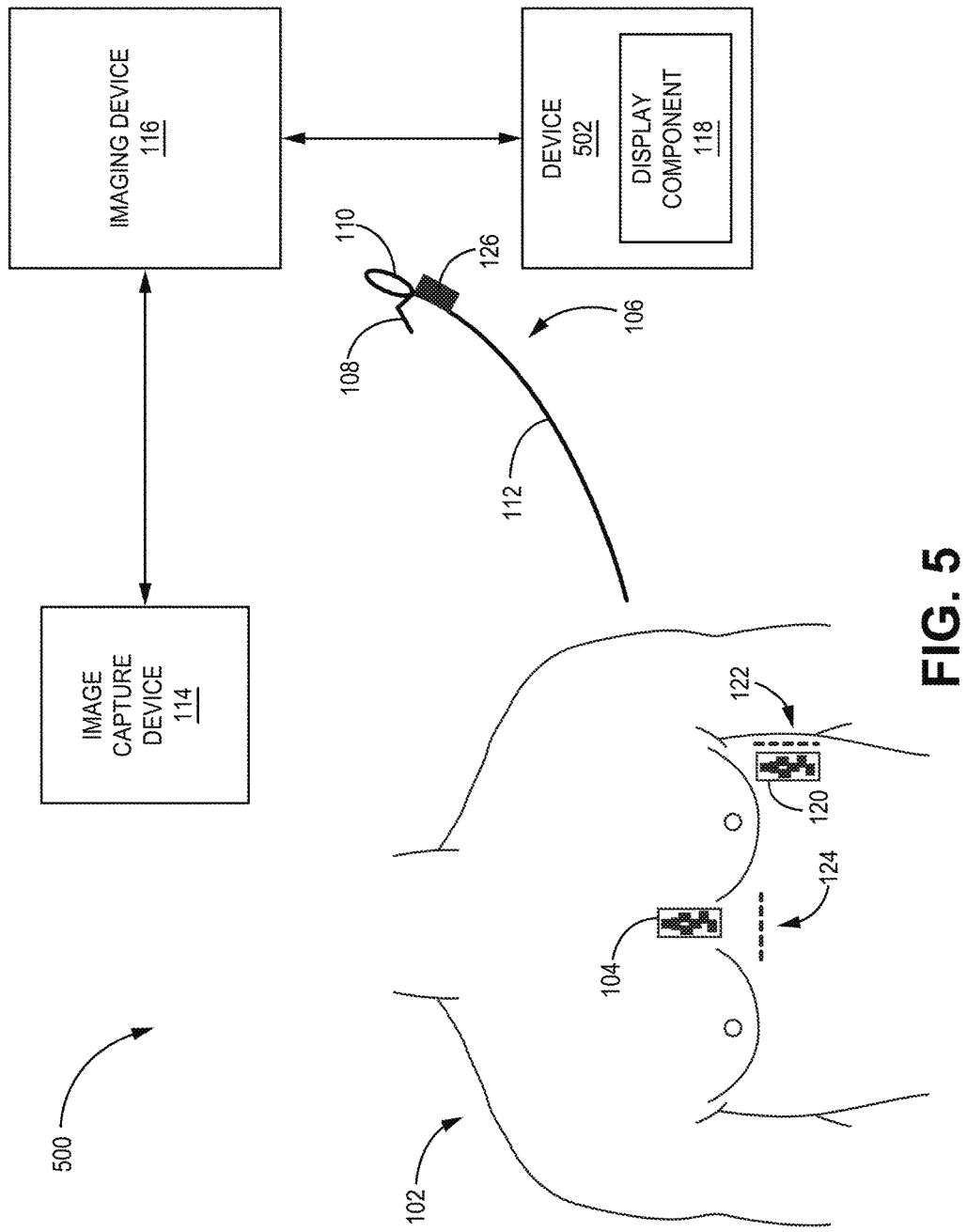
FIG. 5 illustrates a schematic diagram of another example, non-limiting system that facilitates surgery using augmented reality in accordance with one or more embodiments described herein.

FIG. 5 illustrates a schematic diagram of another example, non-limiting system 500 that facilitates surgery using augmented reality in accordance with one or more embodiments described herein. Repetitive description of like elements employed in respective embodiments disclosed herein is omitted for sake of brevity.

As depicted in system 500, the display component 118 can be located remote from the imaging device 116 in another device 502. For example, the imaging device 116 and the device 502 including the display component 118 can be remotely connected via a network and operate according to a server-client relationship. According to this example, the image capture device 114 is also remote from the imaging device 116. The image capture device can capture and provide image data to the imaging device 116 for processing. 2-D and/or 3-D representations generated by the imaging device 116 based on the image data and/or orientation data captured via the orientation unit 126 (in accordance with the mechanisms describe herein) is then sent to device 502 for display by display component 118 (e.g., on a display screen or as a holographic projection).

Figure 6:
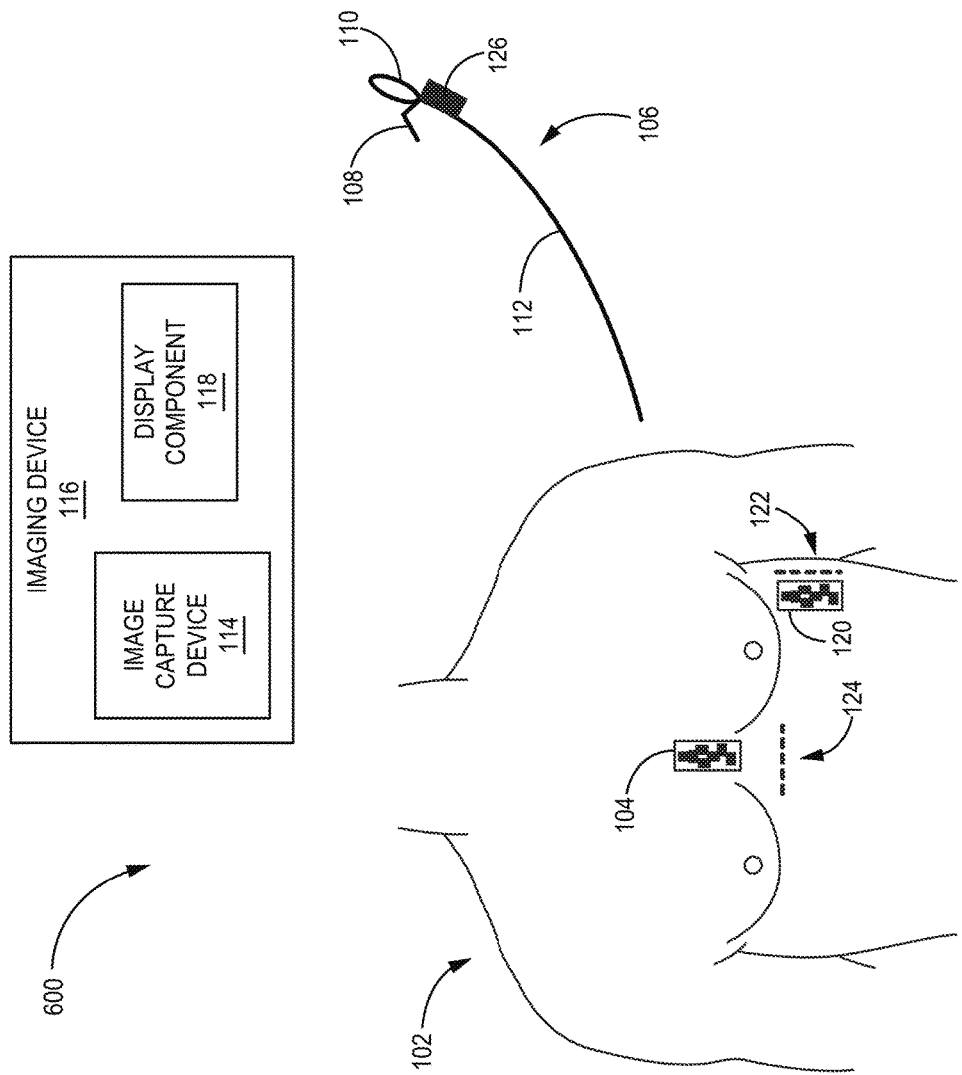
FIG. 6 illustrates a schematic diagram of another example, non-limiting system that facilitates surgery using augmented reality in accordance with one or more embodiments described herein.

FIG. 6 illustrates a schematic diagram of another example, non-limiting system 600 that facilitates surgery using augmented reality in accordance with one or more embodiments described herein. Repetitive description of like elements employed in respective embodiments disclosed herein is omitted for sake of brevity.

As shown in system 600, the imaging device 116, the image capture device 114, and the display component 118 are respectively located on a same device (e.g., a wearable head mount computing device or a goggles/glasses-based wearable computing device). In another embodiment, which is not shown, the image capture device 114 and the display component 118 can be located on the same device while the imaging device 116 is located on another remote device.

With reference to FIGS. 1, 5 and 6, depending on the implementation of the various components or devices of the systems described herein (e.g., systems 100, 500, 600 and the like), one or more of the components or devices can be communicatively coupled via a wireless network or via wired connections. In several exemplary embodiments, one or more of the components and/or devices of the disclosed systems (e.g., orientation unit 126, image capture device 114, imaging device 116, display component 118, and device 502) can be configured to employ various wireless communication protocols to communicate with one another. For example, the orientation unit 126 and the imaging device 116 can communicate using near field communication (NFC). In another example, the orientation unit 126, the image capture device 114, the imaging device, and/or device 502 can communicate using any of various types of other wireless communication protocols. For example, other communication protocols can include, but are not limited to, a BLUETOOTH® technology-based protocol (e.g., BLUETOOTH® low energy (BTLE) protocol), an ultra-wideband (UWB) technology-based protocol, a radio frequency (RF) communication-based protocol, or any other proprietary or non-proprietary communication protocols.

In various embodiments, communication can be facilitated over a personal area network (PAN), a local area network (LAN) (e.g., a Wireless Fidelity (Wi-Fi) network) that can provide for communication over greater distances than the NFC protocol or provide other advantages (e.g., stronger encryption protocols). In some embodiments, the image capture device 114, the imaging device 116 and/or device 502 can communicate with one another and/or another device (e.g., a server device or a tertiary device) over a wide area network (WAN) using cellular or Hyper Text Transfer Protocol (HTTP)-based communication protocols (e.g., session initiation protocol (SIP)).

One or more embodiments of systems 100, 500 and 600 are described in connection with facilitating implantation of a medical device within a patient, e.g., a medical device within a substernal space of the patient, systems using augmented reality. In patients at high risk of ventricular fibrillation, the use of an implantable ICD system has been shown to be beneficial at reducing the likelihood of sudden cardiac death (SCD). An ICD system can include an ICD, which is a battery powered electrical shock device, that may include an electrical housing or an electrode (sometimes referred to as a "can electrode") that is coupled to one or more electrical lead wires placed on or within the heart. If an arrhythmia is sensed, the ICD can send a pulse via the electrical lead wires to shock the heart and restore the normal rhythm of the heart.

Owing to the inherent surgical risks in attaching and replacing electrical leads directly within or on the heart, extravascular ICD systems have been devised to provide shocks to the heart without placing electrical lead wires within the heart or attaching electrical wires directly to the heart. Instead, the extravascular ICD systems can deliver shocks to the heart by the use of a defibrillation lead having electrodes placed subcutaneously between the skin and the ribcage/sternum or electrodes placed substernally (e.g., underneath/below the sternum), or a combination thereof.

Figure 7:
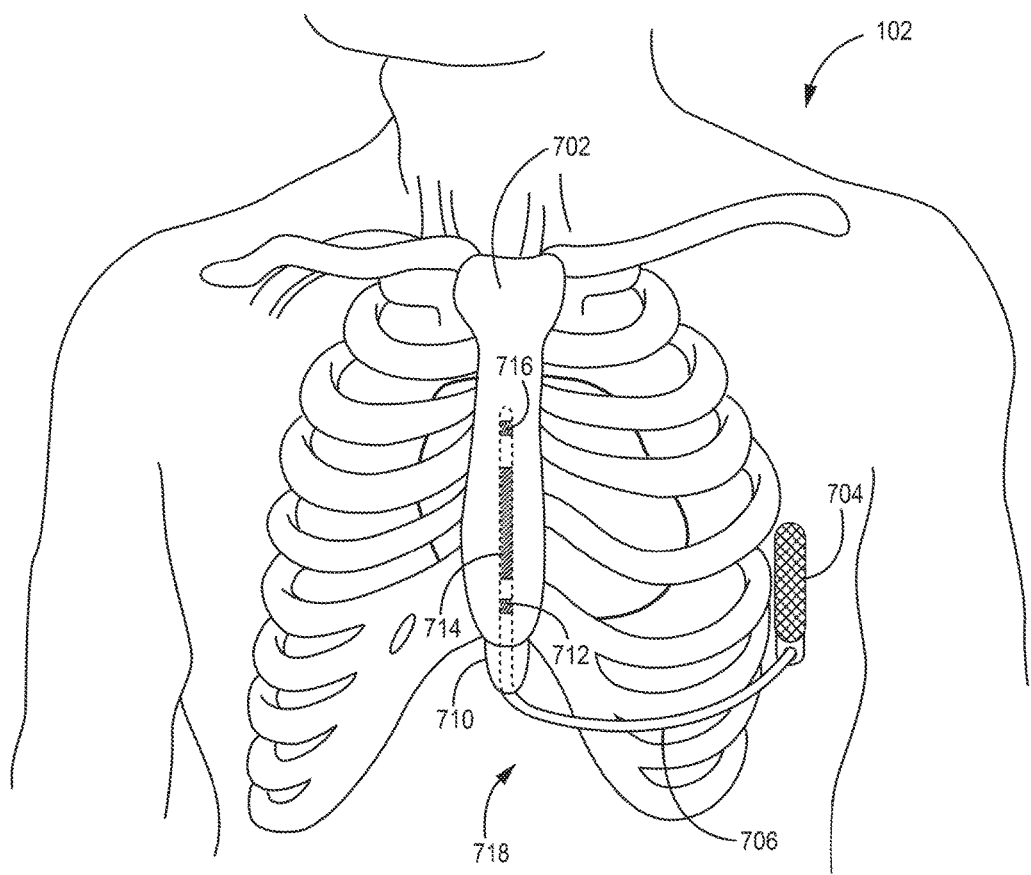
FIG. 7 illustrates a schematic diagram of an example extravascular ICD system implanted within a body of a patient in accordance with one or more embodiments described herein.

FIG. 7 illustrates an example extravascular ICD system 718 implanted within a body 102 of a patient. An extravascular ICD system such as system 718 generally includes an ICD 704 and an electrical lead 706. The ICD 704 is provided in a housing (e.g., a titanium case) containing a battery and electronic circuitry that provides defibrillation therapy and pacing. For example, the housing can house one or more processors, memories, transmitters, receivers, sensors, sensing circuitry, therapy circuitry, power sources and other appropriate components. The ICD 704 can be implanted subcutaneously within the body 102 of the patient, such as on the left midaxillary of the patient above the ribcage (e.g., near the left armpit of the body 102 of the patient). The ICD 704 can also be implanted at other subcutaneous locations on the patient. In some instances, the ICD may alternatively be placed at a substernal location.

The electrical lead 706 includes an elongated body having a proximal end that includes a connector that connects to the ICD 704 and a distal end that includes a plurality of electrodes (e.g., electrodes 712, 714 and 716). When properly implanted, the lead 706 extends subcutaneously above the ribcage from the ICD 704 toward a center of the torso of the patient (e.g., toward the xiphoid process 710 of the patient). For substernal lead placements, at a location near the center of the torso, the lead 706 bends or turns and extends superior under/below the sternum 702 of the patient such that the portion of the lead 706 containing the electrodes 712, 714 and 716 is within the substernal space, including the anterior mediastinum. The anterior mediastinum can include the area within the body 102 being bounded laterally by the pleurae, posteriorly the pericardium, and anteriorly by sternum 702. In some instances, the anterior wall of anterior mediastinum can also be formed by the transversus thoracis and one or more costal cartilages.

The anterior mediastinum includes a quantity of loose connective tissue (e.g., areolar tissue), some lymph vessels, lymph glands, substernal musculature (e.g., transverse thoracic muscle), branches of the internal thoracic artery, and the internal thoracic vein. In one example, the distal portion of lead 706 is configured to be implanted substantially within the loose connective tissue and/or substernal musculature of anterior mediastinum. In other embodiments, the distal portion of the lead 706 can be implanted in other non-vascular, extra-pericardial locations, including the gap, tissue, or other anatomical features around the perimeter of and adjacent to, but not attached to, the pericardium or other portion of heart and not above sternum or ribcage.

Implantation of the lead 706 can be a difficult and intricate procedure, and if done incorrectly or with the improper tools, damage can occur (e.g., especially damage to the heart and/or lungs). In some embodiments, implantation of the substernal lead of the extravascular ICD system involves using a tunneling tool to create a route through the substernal space for the lead 706. For example, a tunneling tool can be used to form the route from the xiphoid process 710 underneath the sternum 702 in the substernal space. A tunneling tool can also be used to create a route from the sternum 702 to the left midaxillary side of the patient above the ribcage when the ICD 704 is implanted (e.g., below the left armpit). After the substernal route is established, the tunneling tool is removed and the lead is fed through the substernal route.

With reference to FIGS. 1, 5, 6 and 7, in accordance with various embodiments described herein, instrument 106 is an example tunneling tool that can be used to create the route for the extravascular lead 706. The tunneling tool can include a stainless steel cylindrical tube featuring an atraumatic distal tip. To create the route, the tunneling tool is inserted (e.g., manually or using a robotic arm) into the body 102 of the patient via an incision (e.g., incision 124 and/or incision 122). The tunneling tool is then advanced through the body 102 of the patient to a target area or end point beneath the sternum 702 and within the anterior mediastinum.

When creating the route through the substernal space, the tunneling tool (e.g., instrument 106) can be carefully maneuvered within the body 102 along a defined route so as to reduce the likelihood of damaging the nerves in the auxiliary region, piercing the lungs, piercing the heart, perforating muscles, routing the tunneling tool between muscle layers, etc. When properly inserted, the tunneling tool can pass under the skin and over the muscles in the torso of the body 102 of the patient to a target area and/or along a target path within the body 102 of the patient.

In accordance with various embodiments, system 100 and the like (e.g., system 500 and system 600) can be configured to facilitate the above described tunneling procedure using the disclosed augmented reality techniques to visualize the tunneling tool relative to internal anatomical structures during insertion and/or advancement of the tunneling tool through the body. For example, a model of the internal anatomical structures within the chest and torso can initially be generated based on previously captured imaging data (e.g., MRI data, X-ray data, fluoroscopy data, etc.) and known structure and components of the patient anatomy (e.g., the human anatomy). The model can include the specific internal anatomical structures that the tunneling tool should avoid as well as the internal anatomical structures that the tunneling tool should be advanced near. In some embodiments, the internal anatomical structures that the tunneling tool should avoid can be visually distinguished (e.g., by a different color or pattern) in the visualization presented via display component 118 from the internal anatomical structures that the tunneling tool should be advanced near.

As the tunneling tool is inserted into the body 102 of the patient via incision 122 and/or 124, the precise position and orientation of the tunneling tool relative to the modeled anatomical structures can be presented to the user via the visualization generated by imaging device 116 and presented via display component 118, in accordance with the aspects and embodiments discussed herein. In some instances, when the tunneling tool is inserted via incision 122 to form a subcutaneous route from the left midaxillary region toward the sternum 702, the tunneling tool can be felt under the skin of the patient. Accordingly, in addition to an augmented reality visualization of the tool provided by system 100 and the like (e.g., system 500 and system 600), a user can manually feel the location of the tool underneath the skin of the patient as the tool is advanced toward the sternum to facilitate guiding the tool to the proper position. However, when forming a route from the xiphoid process 710 (e.g., via incision 124) and beneath the sternum 702 into the substernal space, the sternum 702 and ribcage block the ability of the user to externally feel and guide the tool. Accordingly, by generating and presenting the user with an augmented reality visualization of the tool as it is advanced underneath the sternum 702, the user is able to more accurately form the route for the substernal lead 706 and reduce the likelihood of complications.

In an exemplary embodiment, a sternal fiducial marker 104 can be placed on the body 102 of the patient directly above the sternum 702 and/or at the location where the distal end of the lead 706 should be placed. This sternal fiducial marker 104 can serve as a reference point/object such that the position and orientation of the in-vivo portion of the tunneling tool can be directly correlated to a known reference point (e.g., the position of the sternal fiducial marker 104 relative to a 2-D or 3-D coordinate space can be predetermined) directly above the sternum and/or target location for the distal end of the lead 706. In other embodiments, another incision fiducial marker 120 can be placed on the body 102 of the patient at a known position near the incision 122 (and/or incision 124) where the tunneling tool is inserted. Accordingly, the incision fiducial marker 120 can serve as another reference point/object such that the position and orientation of the in-vivo portion of the tunneling tool can be directly correlated to a known reference point at the incision 122.

Figure 8:
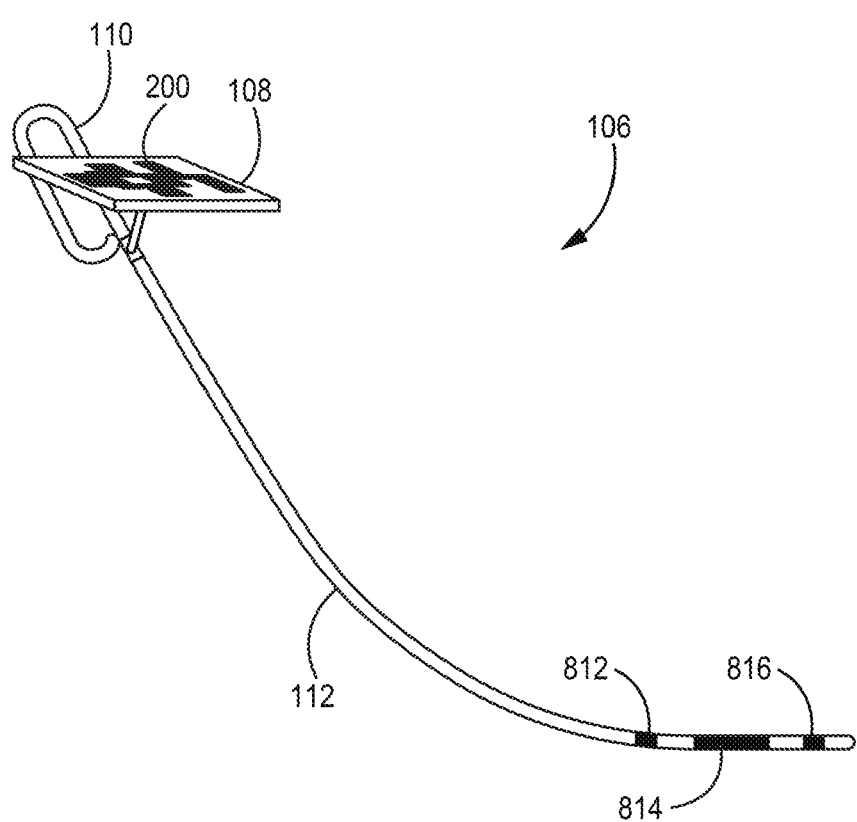
FIG. 8 illustrates a schematic diagram of an example, non-limiting instrument that facilitates surgery using augmented reality in accordance with one or more embodiments described herein.

In another embodiment, the tunneling tool (e.g., instrument 106) can include a set of electrode marks/fiducial markers on a portion of the shaft 112 that corresponds to the locations within the body 102 where the respective electrodes 712, 714, and 716 of the lead 706 should be placed. For example, FIG. 8 illustrates a schematic diagram of another example, non-limiting instrument 106 that facilitates surgery using augmented reality in accordance with one or more embodiments described herein. Repetitive description of like elements described with respective embodiments disclosed herein is omitted for sake of brevity.

With reference to FIGS. 1, 5, 6, 7 and 8, instrument 106 can include a set of electrode markers 812, 814, and 816 located on distal portion of the shaft 112. These electrode markers 812, 814 and 816 can be correlated to locations and/or dimensions of the respective electrodes 712, 714, and 716 of the lead 706. Prior to insertion of the instrument 106 into the patient, the geometry of the instrument can be determined, including the spatial relationships between the respective electrode markers 812, 814, and 816 to one another and the geometrical/spatial relationships between the respective electrode markers 812, 814 and 816 and other points on the instrument that are configured to remain outside the body. For example, the imaging device 116 can capture image data of the instrument 106 and determine the spatial/geometrical relationships between the respective markers to one another and fiducial marker 200.

In accordance with this embodiment, when the distal end of the shaft 112 is inserted into the body 102 of the patient, the imaging device 116 can determine the location of the respective electrode markers 812, 814 and 816 relative to the internal anatomical features of the body 102 based on the predefined geometrical/spatial relationships determined between the electrode markers 812, 814 and 816, and fiducial marker 200 (and/or other points on the instrument 106 configured to remain outside of the body), and a predetermined geometrical/spatial relationship between fiducial marker 200 relative to one or more reference points/markers not located on the instrument (e.g., a body part, an external fiducial marker such as fiducial marker 104, etc.). As a result, imaging device 116 can generate a visualization depicting the locations of the respective electrode markers 812, 814 and 816 beneath the sternum 702 to facilitate aligning the electrode markers 812, 814 and 816 with the correct anatomical features within the body 102 where the electrodes 712, 714 and 716 of the lead 706 should be placed.

Although various embodiments of augmented reality assisted surgery are described herein in connection with performing extravascular ICD implantation, it should be appreciated that the disclosed embodiments are not limited to surgery involving extravascular ICD implantation. For example, the disclosed embodiments can be applied to various types of surgical procedures involving an instrument 106 that is inserted into the body, especially procedures in which cutting or opening of the body 102 of the patient is employed to visualize the surgical area being treated or addressed. In addition, it should be noted that the disclosed systems, methods, and computer readable media may not be limited to treatment of a human patient. In alternative examples, the disclosed embodiments can be implemented in non-human patients, e.g., primates, canines, equines, pigs, ovines, bovines, and felines. For example, these animals can undergo clinical or research therapies that may benefit from the subject matter of this disclosure. Finally, the disclosed embodiments can be used to assist actual surgery, exploratory surgery, or simulated surgery performed on non-live or model cadavers for training and procedural development purposes.

Figure 9:
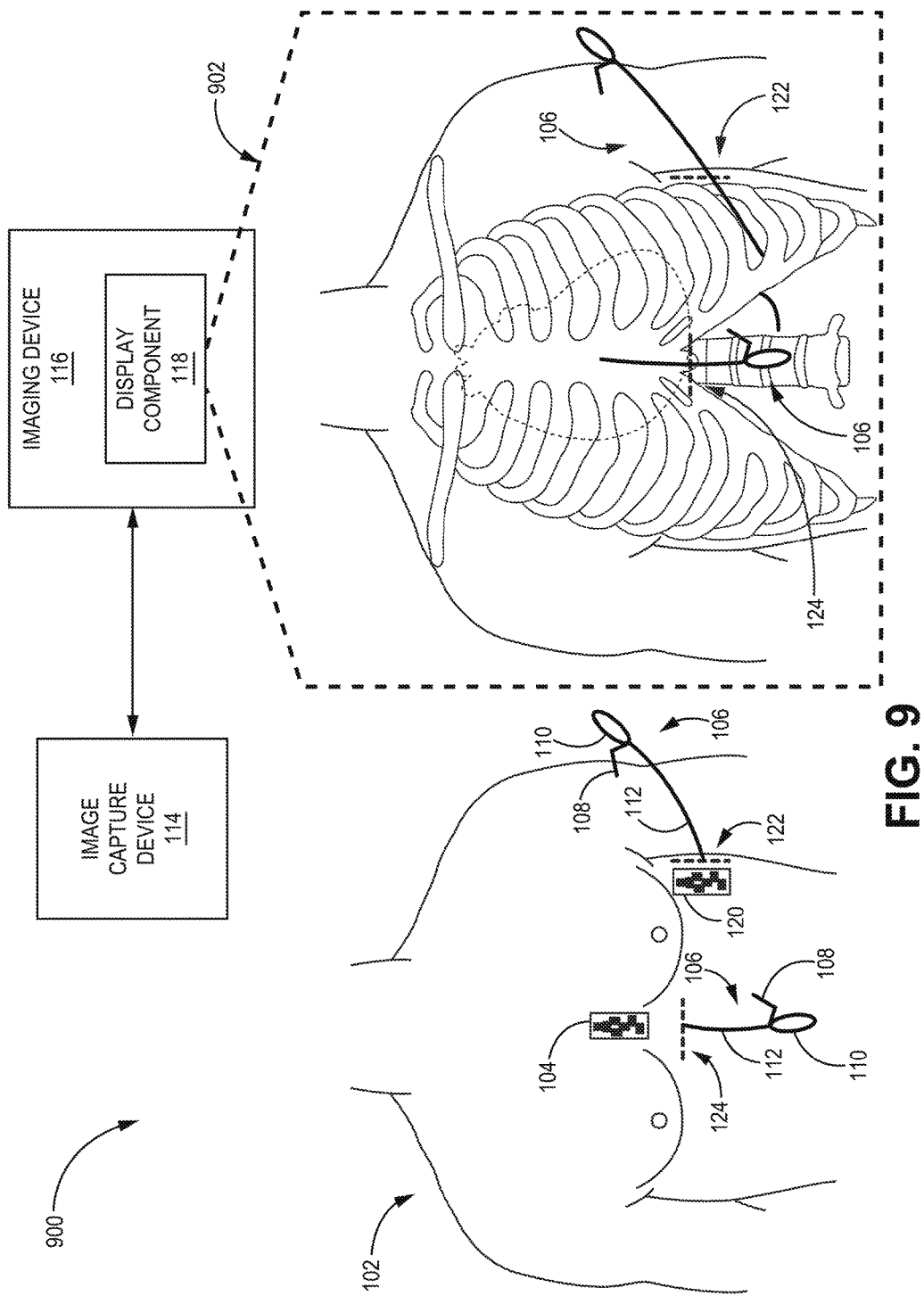
FIG. 9 illustrates a schematic diagram of another example, non-limiting system that facilitates surgery using augmented reality in accordance with one or more embodiments described herein.
Figure 10:
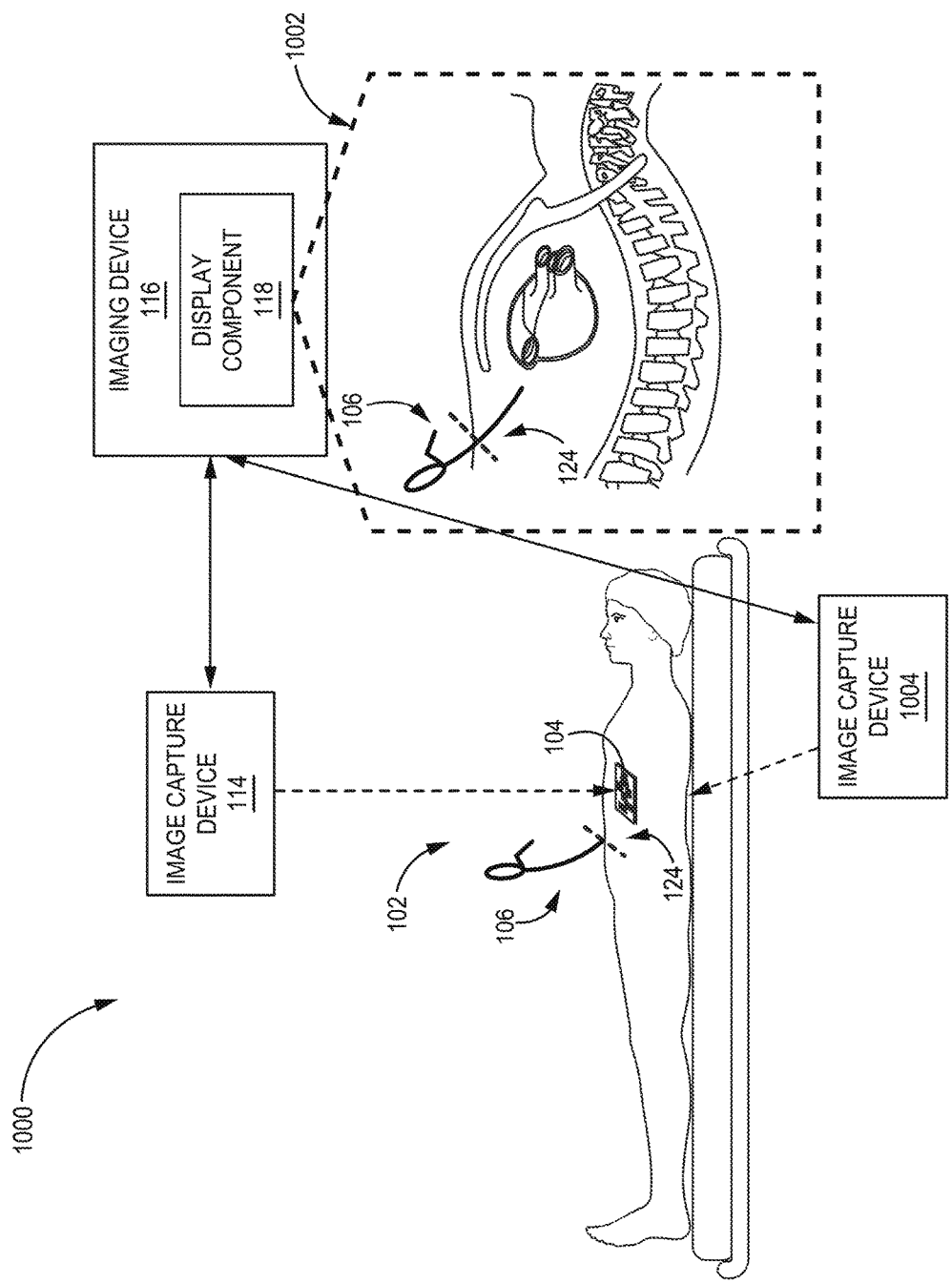
FIG. 10 illustrates a schematic diagram of another example, non-limiting system that facilitates surgery using augmented reality in accordance with one or more embodiments described herein.
Figure 11:
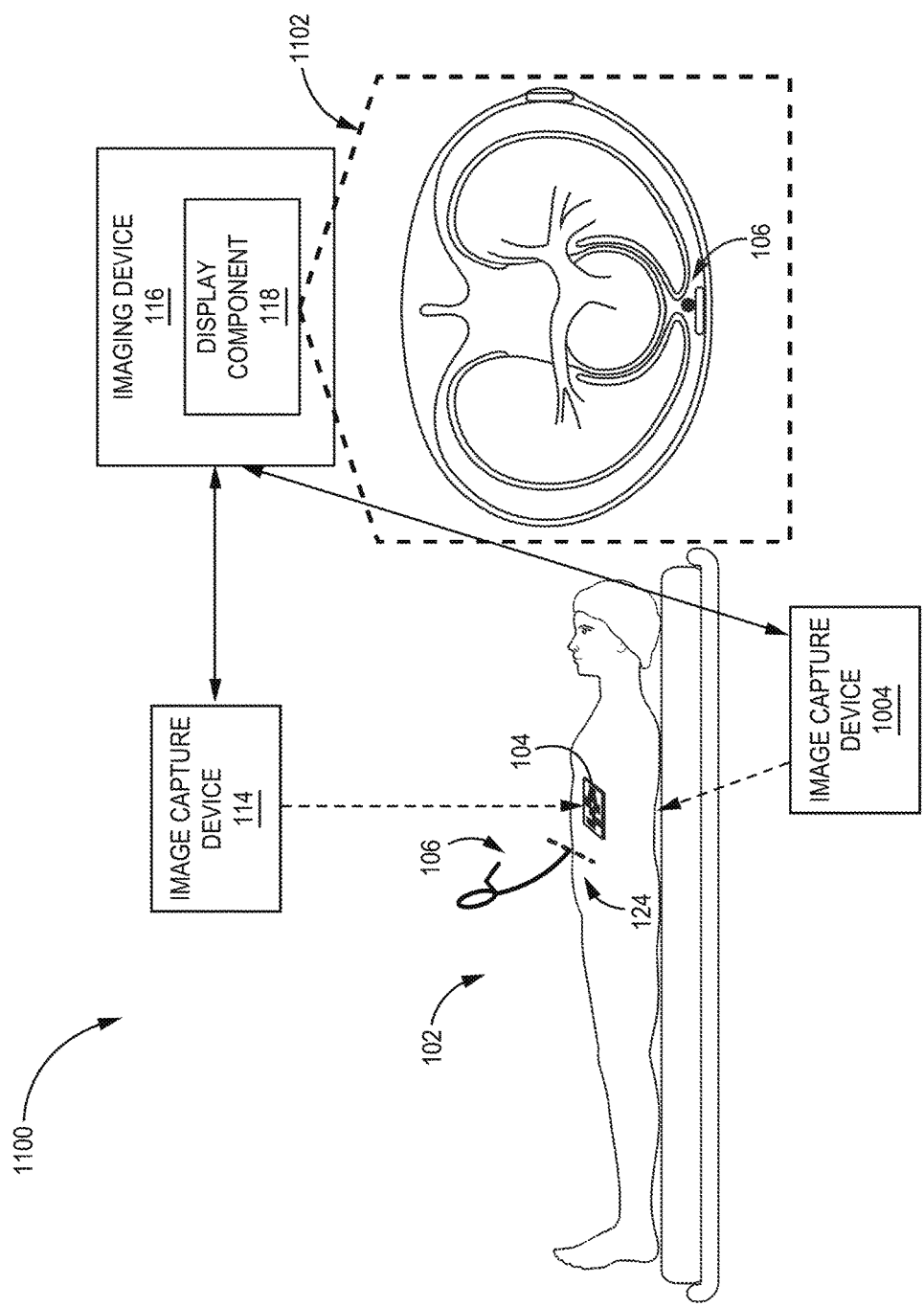
FIG. 11 illustrates a schematic diagram of another example, non-limiting system that facilitates surgery using augmented reality in accordance with one or more embodiments described herein.

FIGS. 9-11 illustrate schematic diagrams of example, non-limiting systems 900, 1000, and 1100 that facilitate surgery using augmented reality in accordance with one or more embodiments described herein. Systems 900, 1000, and 1100 demonstrate the features and functionalities of systems 100, 500, 600. Systems 900, 1000, and 1100 include example respective visualizations 902, 1002 and 1102 generated by imaging device 116 and/or rendered via display component 118 based on image data captured via image capture device 114 and/or image capture device 1004 during insertion of instrument 106 into the patient via incision 124 and/or 122, in accordance with the various embodiments disclosed herein. The example visualizations respectively include internal structures of the patient 102 relative to a current position and orientation of a portion of the instrument 106. Repetitive description of like elements employed in respective embodiments is omitted for sake of brevity.

With reference to FIG. 9, illustrated is an example system 900 showing a visualization 902 of a body 102 of a patient, as depicted to the left of the visualization 902, with an instrument 106 inserted into incision 124 and incision 122. Visualization 902 provides a top down perspective of internal structures of the chest/torso with the instrument 106 inserted. In an exemplary embodiment, visualization 902 is a 3-D model. In other embodiments, visualization 902 can be depicted as a 2-D model. As shown in visualization 902, the in-vivo portions of the instrument 106 relative to internal structures of the body and incisions 124 and 122 are presented.

FIG. 10 illustrates another example visualization 1002 of an actual body 102 of a patient, as depicted to the left of the visualization 1002, with an instrument 106 inserted into incision 124. Visualization 1002 provides a side view perspective of internal structures of the chest/torso with instrument 106 inserted. To facilitate generating this side view perspective, system 1000 can include image capture device 114 positioned above the patient and pointed substantially perpendicular relative to the operating area, and another image capture device 1004 positioned on a side of the patient and substantially coplanar with the operating area. Image capture device 1004 can include the features and functionality of image capture device 114 as described with respect to FIG. 1. In an exemplary embodiment, visualization 1002 is a 3-D model. In other embodiments, visualization 1002 can be depicted as a 2-D model. As shown in visualization 1002, the in-vivo portion of the instrument 106 relative to internal structures of the body and incision 124 is presented.

FIG. 11 illustrates another system 1100 showing a visualization 1102 of a body 102 of a patient, as depicted to the left of the visualization 1102, with an instrument 106 inserted into incision 122. Visualization 1102 provides a cross-sectional or transverse view of internal structures of the chest/torso with instrument 106 inserted. To facilitate generating this transverse view perspective, system 1100 can include image capture device 114 positioned above the patient and pointed substantially perpendicular relative to the operating area, and another image capture device 804 positioned on a side of the patient and substantially coplanar with the operating area. In an exemplary embodiment, visualization 1102 is a 2-D model. For example, in an exemplary embodiment, visualization 1102 is an orthographic projection of a transverse cross-section of the chest at a position above the sternal space. In other embodiments, visualization 1102 can be depicted as a 3-D model. As shown in visualization 1102, the in-vivo portion of the instrument 106 relative to internal structures of the body is presented (e.g., as the black dot).

Figure 12:
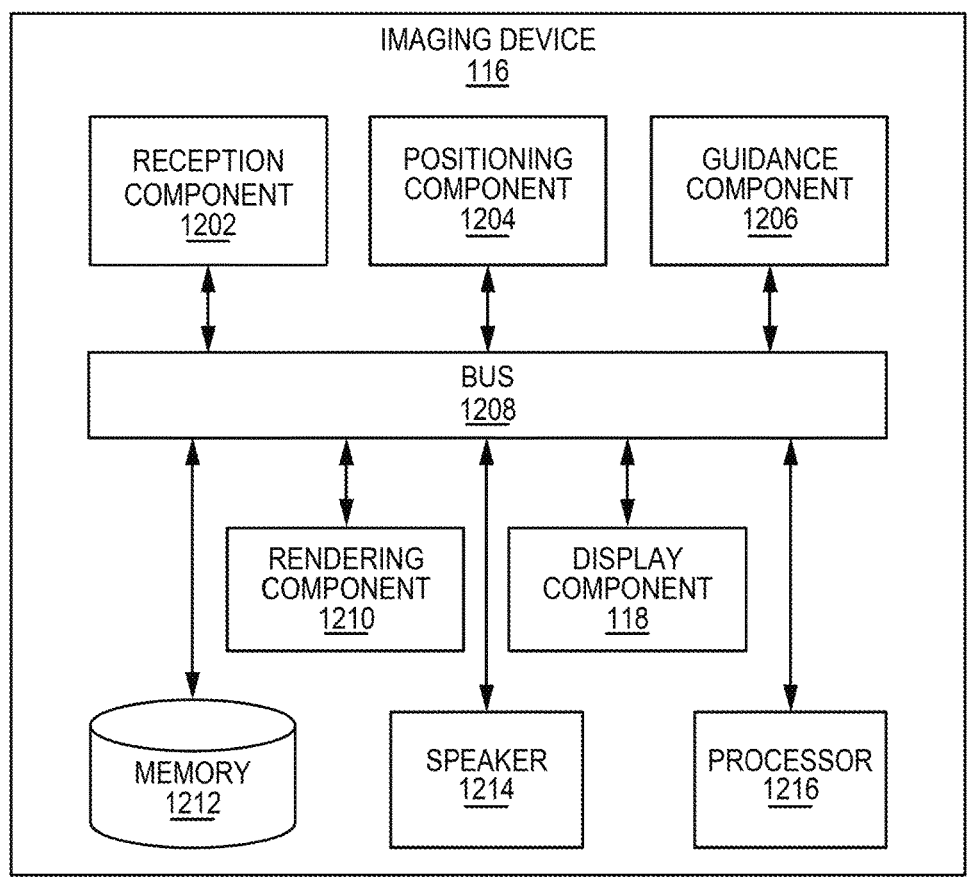
FIG. 12 illustrates a block diagram of an example, non-limiting imaging device facilitating surgery using augmented reality in accordance with one or more embodiments described herein.

FIG. 12 illustrates a block diagram of an example, non-limiting imaging device facilitating surgery using augmented reality in accordance with one or more embodiments described herein. Repetitive description of like elements employed in other embodiments described herein is omitted for sake of brevity.

In addition to display component 118, imaging device 116 can include reception component 1202, positioning component 1204, guidance component 1206, rendering component 1210, memory 1212, speaker 1214, and processor 1216. Memory 1212 can store computer executable components, and processor 1216 that executes the computer executable components stored in the memory (e.g., reception component 1202, positioning component 1204, guidance component 1206, rendering component 1210, and software components of display component 1218). Imaging device 116 can further include a bus 1208 that couples the various components including, but not limited to, reception component 1202, positioning component 1204, guidance component 1206, rendering component 1210, display component 1218, memory 1212, speaker 1214, and processor 1216.

Reception component 1202 can be configured to receive image data captured by one or more image capture devices (e.g., image capture device 114 and the like) and orientation data captured via an orientation unit 126 attached to instrument 106. Reception component 1202 can also receive predetermined, known and/or defined information/data that facilitates determining the position and orientation of an in-vivo portion of an instrument and generating visualizations of the instruments relative to anatomical structures of the patient. For example, reception component 1202 can receive predetermined, defined, known or preconfigured virtual models of a patient, defined coordinate positions of one or more reference objects/points relative to a 2-D or 3-D coordinate space corresponding to the operating environment, information identifying fiducial marker patterns, information identifying the geometry, size and/or shape of a instrument 106 to be tracked during a surgical procedure, etc. Information received by reception component 1202 can be processed by the imaging device 116 and/or stored in memory 1212.

Positioning component 1204 can be configured to determine positions and orientations of an in-vivo portion of an instrument 106 relative to one or more anatomical features of the patient based on the information received by reception component 1202, as described in detail with respect to FIG. 1. For example, positioning component 1204 can determine relative positions of an internal portion of the instrument inserted into a body 102 of the patient relative to one or more anatomical structures of the body 102 based on a known or determined size and shape of the instrument and image data including, but not limited to, a fiducial marker or portion of the fiducial marker on the instrument, an external part of the body, another fiducial marker located on an external part of the body or the like.

Rendering component 1210 can be configured to generate 2-D and/or 3-D visualizations including a representation of the instrument 106 at a determined position and orientation of the instrument 106 relative to one or more modeled anatomical structures of the body corresponding to an actual position and orientation of the instrument 106 relative to the actual anatomical structures of the body 102. For example, rendering component 1210 can generate and/or configure visualizations 902, 1002 and 1102. The visualizations generated or configured by rendering component 1210 can further be displayed or presented via a graphical user interface, or as a hologram by, display component 118.

Guidance component 1206 can be configured to provide guidance to a user during insertion and/or maneuvering of an instrument 106 within a body 102 of a patient based on the determined positions and orientations of the instrument 106 relative to internal anatomical structures of the body, and/or based on previously determined parameters or metrics regarding how and where the instrument 106 should be inserted, maneuvered, oriented and positioned during the particular procedure being performed. For example, in an embodiment directed to employing instrument 106 to create a route for insertion of the extravascular lead 706, guidance component 1206 can be provided access to information (e.g., in memory 1212 or at another device) identifying an optimal route via which the instrument 106 should advance within the body 102 of the patient. For example, the information can identify respective points along a 2-D or 3-D coordinate space corresponding to the internal structure of the body 102 of the patient. The information can also identify precise distances (e.g., in centimeters or millimeters) relative to certain internal anatomical structures from which the instrument 106 should be located at respective points along the route. The information can also identify internal structures that the instrument 106 should avoid contacting and/or distances that the instrument 106 should be located from relative to these internal structures during insertion into the body 102.

In an embodiment, guidance component 1206 can track the positions and orientations of the instrument 106 as it is inserted to determine a trajectory path of the instrument 106. According to this embodiment, guidance component 1206 can compare a current trajectory path for the instrument 106 with an optimal route for the instrument 106 to determine whether the instrument 106 is on the proper track. In response to a determination that the instrument 106 is off course, the guidance component 1206 can provide the user with instruction that facilitates aligning the instrument 106 back on the proper track. For example, guidance component 1206 can direct rendering component 1210 to draw a virtual line on a visualization corresponding to the correct track and another virtual line corresponding to the current off target trajectory of the instrument 106.

In another example, guidance component 1206 can determine how to adapt the current position and/or orientation of the instrument 106 to bring the instrument 106 onto the proper track. For instance, guidance component 1206 can determine that the instrument 106 should move a defined number of centimeters to the right or left, and/or another defined number of centimeters up or down, etc.

The guidance component 1206 can further provide these instructions to the user in a visual format (e.g., as text, arrows, or other visual cues presented with the visualization) and/or an audible format (e.g., as spoken instructions output via the speaker 1214). Guidance component 1206 can also determine when the instrument 106 is near or heading toward an anatomical feature that should be avoided by the instrument 106 (e.g., the heart, the ribs, etc.). The guidance component 1206 can further provide instruction notifying the user of the incorrect and dangerous trajectory to prevent injury to the patient.

Figure 13:
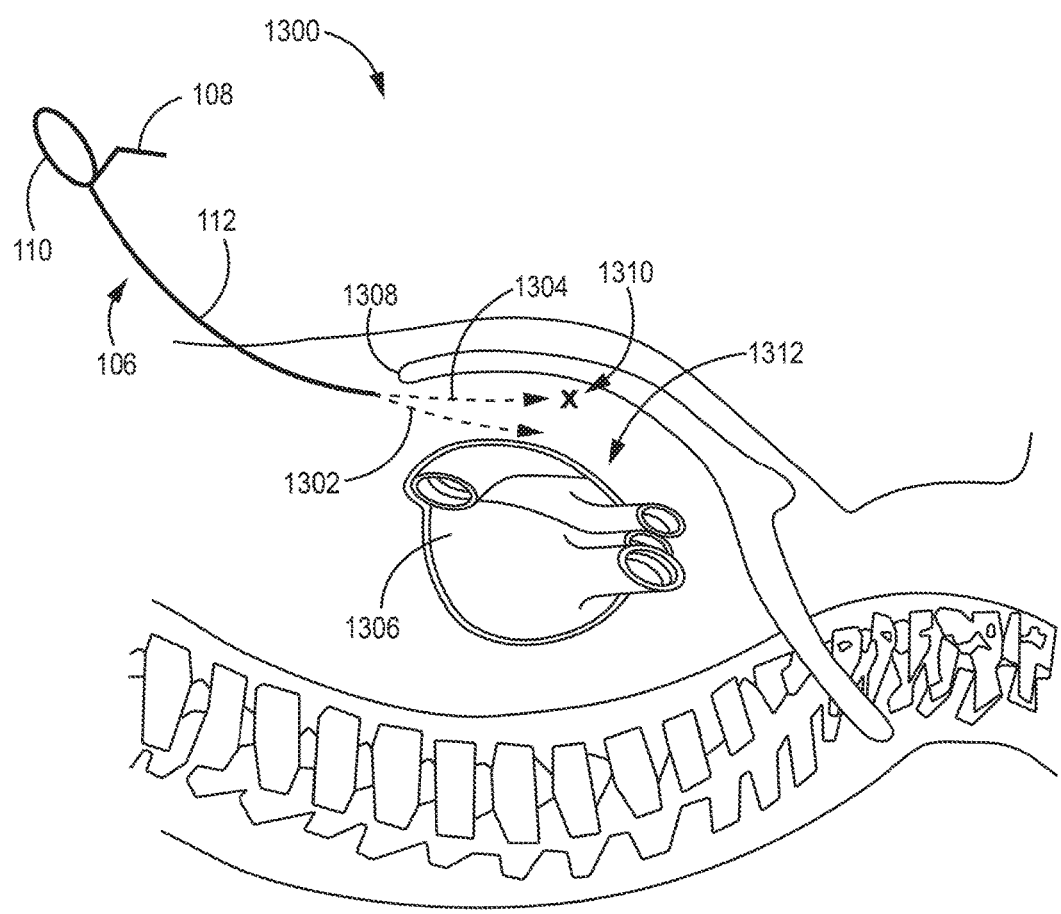
FIG. 13 illustrates a schematic diagram of an example, non-limiting visualization that facilitates surgery using augmented reality in accordance with one or more embodiments described herein.

FIG. 13 illustrates a schematic diagram of an example, non-limiting visualization 1300 that facilitates surgery using augmented reality in accordance with one or more embodiments described herein. In some embodiments, visualization 1300 can include the same or similar features as visualization 1002. Repetitive description of like elements employed in respective embodiments disclosed herein is omitted for sake of brevity.

Visualization 1300 can illustrate various visual guidance features afforded by guidance component 1206. In particular, visualization 1300 can include a first trajectory line 1302 extending from the distal end of the instrument 106 indicating the current trajectory path of the instrument 106. Visualization 1300 can also include a second trajectory line 1304 corresponding to the correct or optimal trajectory path for advancement of the instrument 106. By looking at visualization 1300, the user operating the instrument 106 can clearly see that the instrument 106 is off course and maneuver the instrument 106 to the correct course (e.g., second trajectory line 1304).

Visualization 1300 can also include a target mark 1310 that indicates a target end position for the instrument 106. For example, with respect to formation of a substernal route for implantation of an extravascular lead, the target mark 1310 is located below the sternum 1308 within an area of the anterior mediastinum 1312 between the sternum 1308 and the heart 1306. In some embodiments, guidance component 1206 can further provide visual and/or audible instruction informing the user of positions (e.g., in actual centimeters, millimeters or any other units that are appropriate) the instrument 106 is located relative to target mark 1310 and the identified anatomical structures.

Figure 14A:
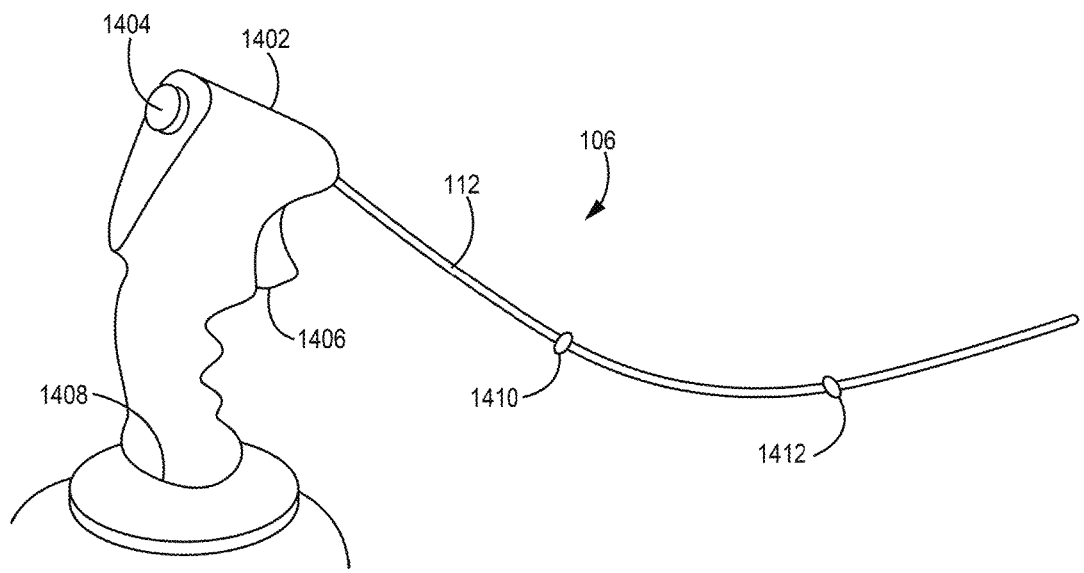
FIGS. 14A and 14B illustrate schematic diagrams of example, non-limiting instruments that facilitate surgery using augmented reality in accordance with one or more embodiments described herein.
Figure 14B:
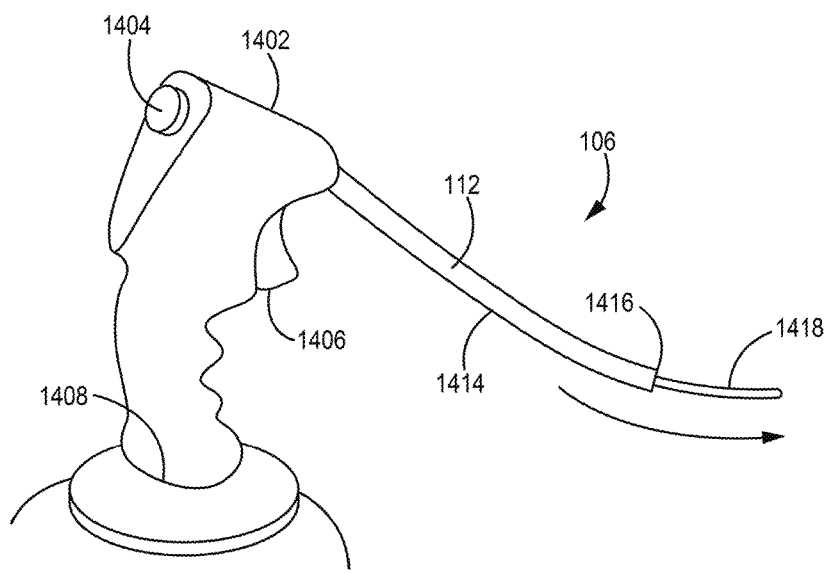

FIGS. 14A and 14B illustrate schematic diagrams of example, non-limiting instruments that facilitate surgery using augmented reality in accordance with additional embodiments described herein. Repetitive description of like elements employed in respective embodiments disclosed herein is omitted for sake of brevity.

Similar to previously described embodiments, the instrument 106 depicted in FIGS. 14A and 14B includes an elongated shaft 112 configured to insert inside the body of a patient. The elongated shaft 112 can have a curved geometry to facilitate forming a substernal route in some implementations. In accordance with the embodiments depicted in FIGS. 14A and 14B, the handle 110 previously described (e.g., in FIG. 1) has been replaced with a handgrip 1402 that facilitates mechanically controlling the position, orientation and/or configuration of the elongated shaft 112. For example, as depicted in FIG. 14A, in one embodiment, the elongated shaft 112 can have one or more articulation joints (e.g., articulation joints 1410 and 1412) that allow portions or sections of the elongated shaft separated by the articulation joints to mechanically pivot or rotate relative to one another. The manner of movement enabled by the articulation joints can vary. For example, the articulation joints 1410 and 1412 can include, but are not limited to, a ball and socket joint, a hinge joint, a condyloid joint (a joint that permits all forms of angular movement except axial rotation), a pivot joint, gliding joint, and/or a saddle joint.

In another example, as depicted in FIG. 14B, the length of the elongated shaft 112 can be dynamically adapted via mechanical movement of different segments (e.g., segments 1414 and 1418) of the elongated shaft 112 relative to one another. For instance, the elongated shaft 112 can include two or more attached segments 1414 and 1418, wherein at least one of the segments is configured to insert into the other and extend away from and retract back into the other segment in a telescope manner. For example, segment 1418 is depicted with a smaller radius than segment 1414 and extending outward from segment 1414. According to this example, segment 1418 is configured to be able to further extend a defined length outward from segment 1414 and/or retract back into segment 1414.

In one or more implementations, the handgrip 1402 can include one or more manual control input components (e.g., control button 1404, trigger button 1406, joystick control 1408) that can facilitate manually controlling movement and/or configuration of the elongated shaft 112 based on the mechanical configuration of the elongated shaft enabled by the articulation joints (e.g., articulation joints 1410 and 1412) and/or the retractable segments (e.g., segment 1418). For example, the instrument 106 can include a motor (not shown) and electrical circuitry (not shown) coupling the one or more input components, the motor, and/or the different segments and/or joints of the elongated shaft 112. The motor can be configured to respond to control instruction input received from the one or more manual input control components to cause the elongated shaft 112 to move in a manner defined by the control instruction input. For example, with reference to FIG. 14A, the trigger button 1406 can be configured to direct a segment of the elongated shaft 112 to move up relative to an articulation joint (e.g., articulation joint 1410 or 1412), the control button 1404 can be configured to direct the segment to move down relative to the articulation joint, and/or the joystick control 1408 can be configured to direct the segment to move left and right relative to the articulation joint. In another example, with reference to FIG. 14B, the trigger button 1406 can be configured to direct segment 1418 to extend outward from segment 1414 and/or the control button 1404 can be configured to direct segment 1418 to retract into segment 1414.

With reference to FIGS. 14A, 14B, 1 and 10, in various embodiments, the instrument 106 can be communicatively coupled to imaging device 116, either via one or more wires or wirelessly. The instrument 106 can also include a power source to facilitate mechanical and electrical operation of the instrument 106, and/or be coupled to an external power source via one or more wires (e.g., a power source provided by imaging device 116 and/or another device). The instrument 106 can be further configured to provide the imaging device 116 with the control input information that defines the input control instructions applied to the instrument via the one or more input control components (e.g., control button 1404, trigger button 1406 and joystick control 1408).

According to these embodiments, the imaging device 116 can be configured to receive the control input information (e.g., via reception component 1202) and map the control input information to a configuration of the elongated shaft 112. For example, the positioning component 1204, can determine a current configuration of the elongated shaft 112 relative to a default configuration of the elongated shaft 112 based on the changes to the configuration of the elongated shaft 112 caused by the control input information. The positioning component 1204 can further determine a position and/or configuration of the instrument 106 and the elongated shaft 112 relative to the body 102 of the patient and one or more internal anatomical features of the patient based on the determined configuration of the elongated shaft 112, a position and/or orientation of the handgrip 1402 portion of the instrument 106 that is outside of the body 102 (e.g., using the various imaging positioning techniques described herein) and/or a known configuration of the entire instrument 106 (e.g., a known configuration of the handgrip 1402 portion relative to the elongated shaft 112 portion). The rendering component 1210 can then generate 2-D and/or 3-D visualizations of the elongated shaft 112 at the determined position, orientation and/or configuration inside the body 102 relative to the one or more anatomical features as, previously described.

Figure 15:
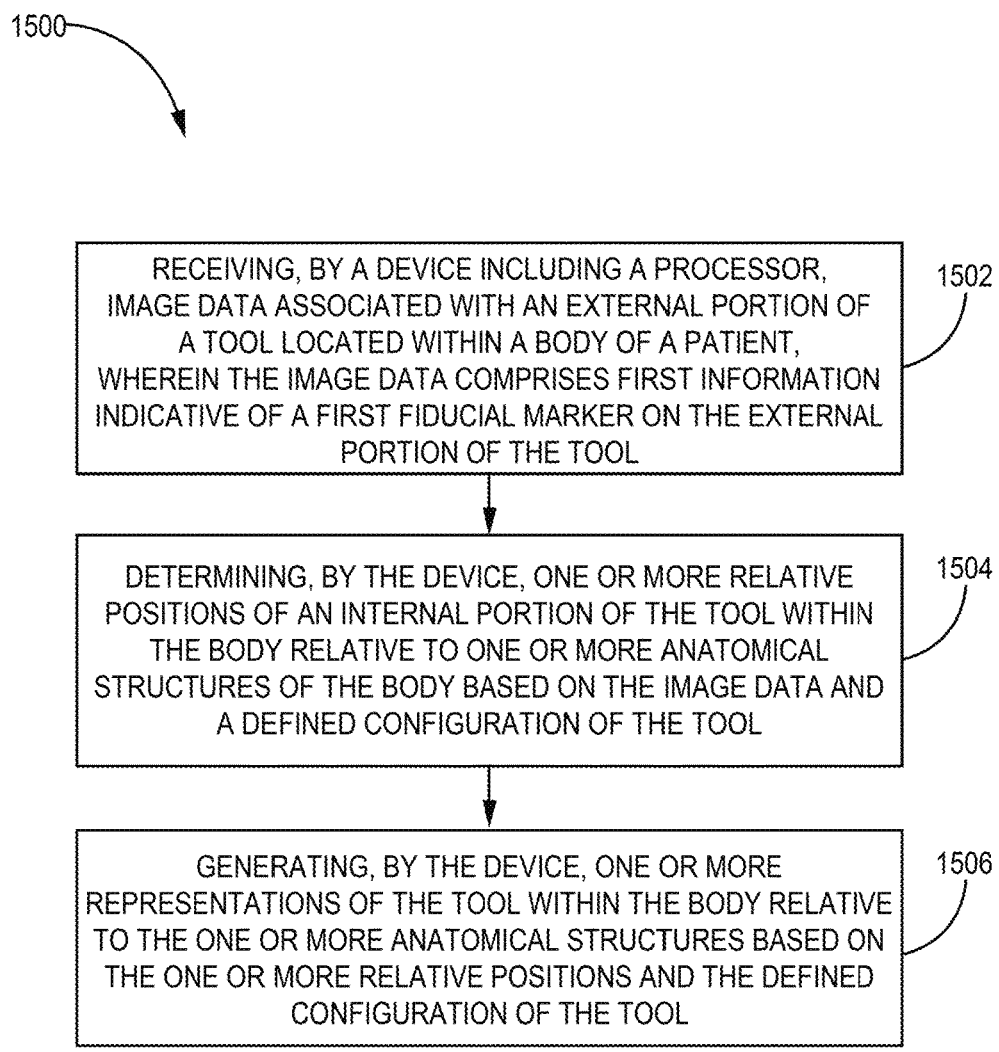
FIG. 15 illustrates a flow diagram of an example, non-limiting method facilitating surgery using augmented reality in accordance with one or more embodiments described herein.
Figure 16:
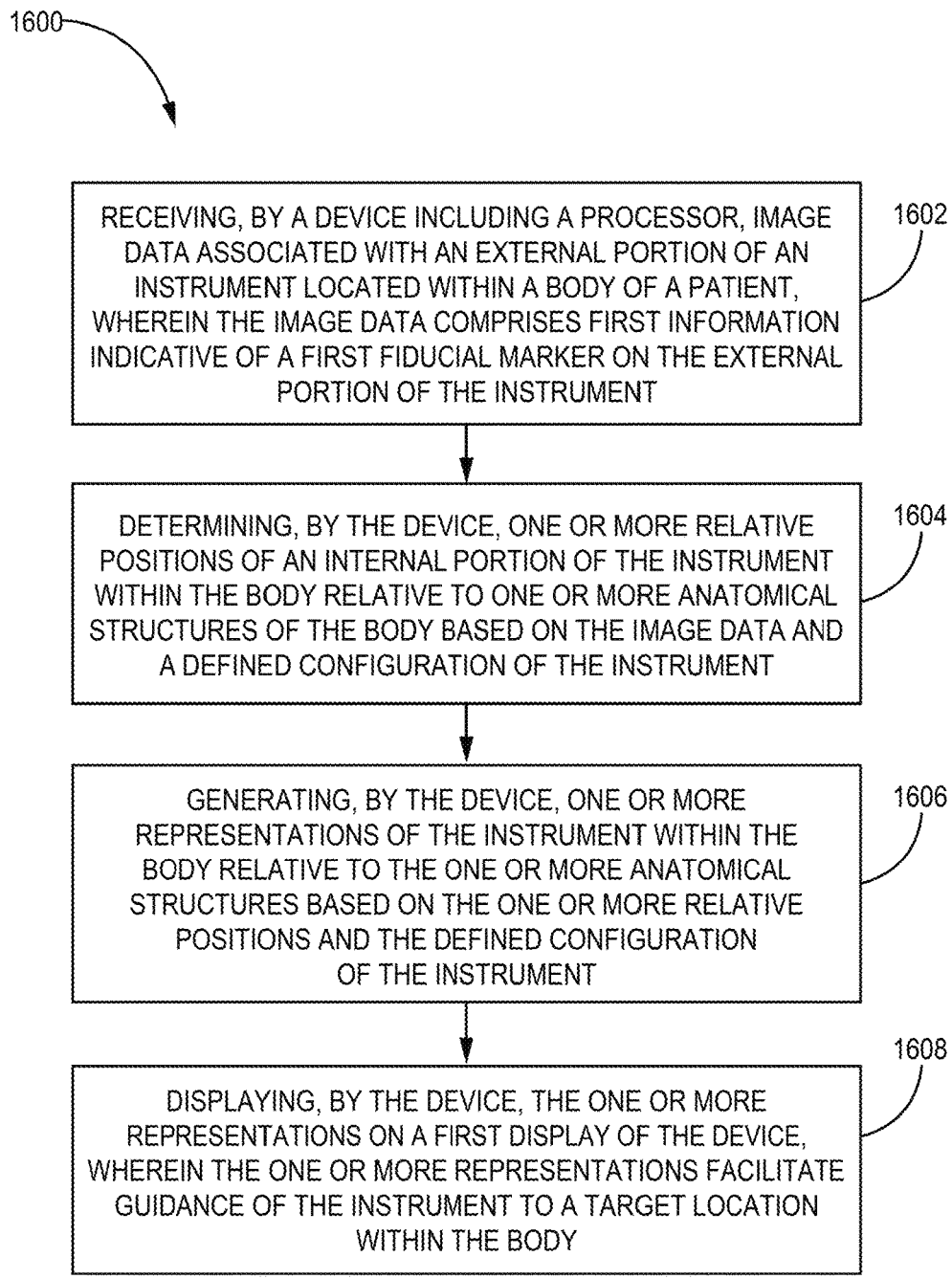
FIG. 16 illustrates a flow diagram of another example, non-limiting method facilitating surgery using augmented reality in accordance with one or more embodiments described herein.
Figure 17:
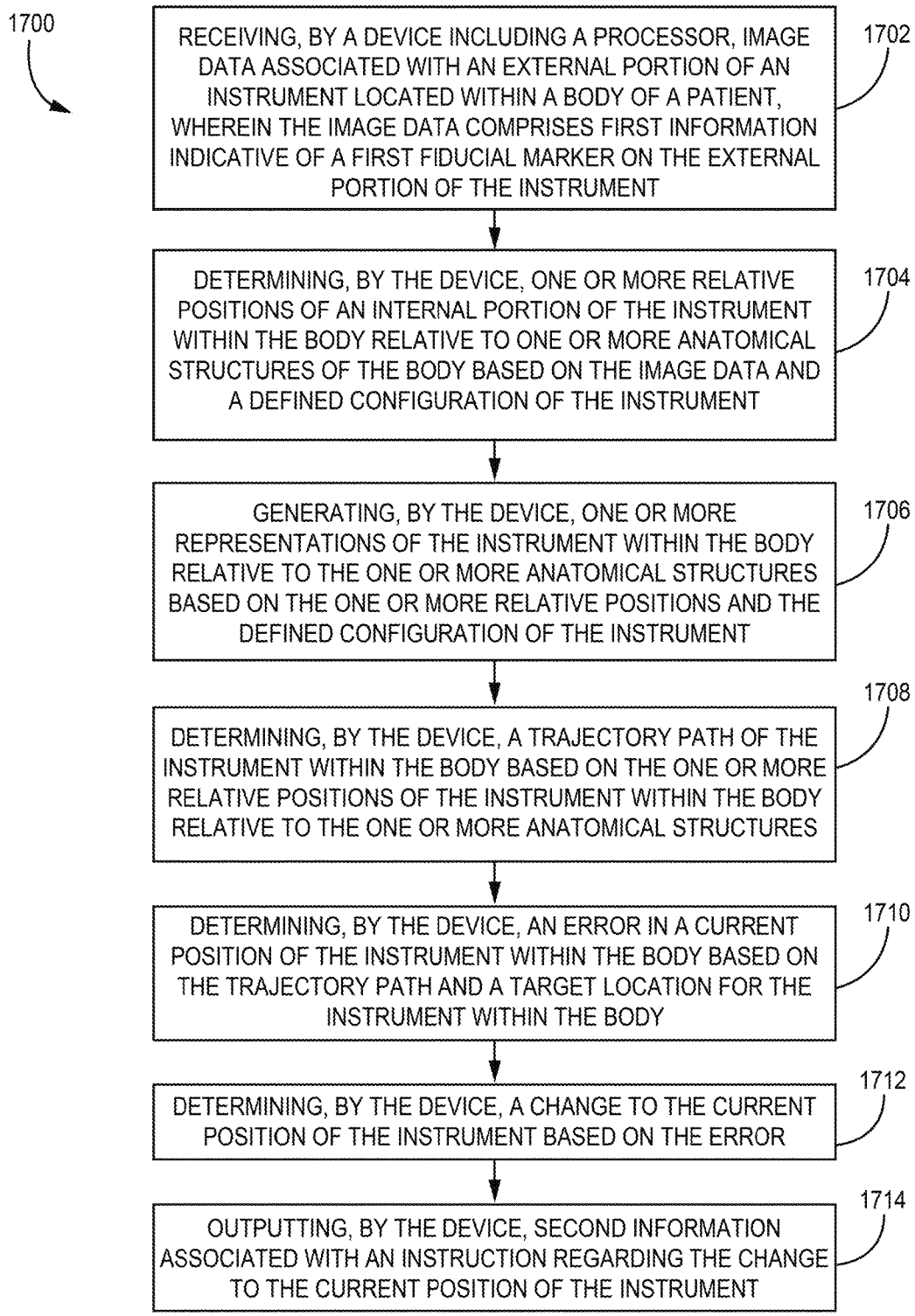
FIG. 17 illustrates a flow diagram of another example, non-limiting method facilitating surgery using augmented reality in accordance with one or more embodiments described herein.

In view of the example systems and/or devices described herein, example methods that can be implemented in accordance with the disclosed subject matter can be further appreciated with reference to flowcharts in FIGS. 15-17. Repetitive description of like elements employed in respective embodiments is omitted for sake of brevity.

For purposes of simplicity of explanation, example methods disclosed herein are presented and described as a series of acts; however, it is to be understood and appreciated that the disclosed subject matter is not limited by the order of acts, as some acts may occur in different orders and/or concurrently with other acts from that shown and described herein. For example, a method disclosed herein could alternatively be represented as a series of interrelated states or events, such as in a state diagram. Moreover, interaction diagram(s) may represent methods in accordance with the disclosed subject matter when disparate entities enact disparate portions of the methods. Furthermore, not all illustrated acts may be required to implement a method in accordance with the subject specification. It should be further appreciated that the methods disclosed throughout the subject specification are capable of being stored on an article of manufacture to facilitate transporting and transferring such methods to computers for execution by a processor or for storage in a memory.

FIG. 15 illustrates a flow diagram of an example, non-limiting method 1500 facilitating surgery using augmented reality in accordance with one or more embodiments described herein. At 1502, a device (e.g., imaging device 116) including a processor can receive image data associated with an external portion of a tool located within a body of a patient. The image data can include first information indicative of a first fiducial marker on the external portion of the tool. At 1504, the device can determine one or more relative positions of an internal portion of the tool within the body relative to one or more anatomical structures of the body based on the image data and a defined configuration (e.g., known size and shape) of the tool. At 1506, the device can generate one or more representations of the tool within the body relative to the one or more anatomical structures based on the one or more relative positions and the defined configuration of the tool. For example, the representations can respectively correspond to different positions, orientation, and perspectives of the tool relative to the one or more anatomical structures over the course of surgery.

FIG. 16 illustrates a flow diagram of another example, non-limiting method 1600 facilitating surgery using augmented reality in accordance with one or more embodiments described herein. At 1602, a device (e.g., imaging device 116) including a processor can receive image data associated with an external portion of an instrument (e.g., instrument 106) located within a body of a patient. The image data can include first information indicative of a first fiducial marker on the external portion of the instrument. At 1604, the device can determine one or more relative positions of an internal portion of the instrument within the body relative to one or more anatomical structures of the body based on the image data and a defined configuration of the instrument. At 1606, the device can generate one or more representations of the instrument within the body relative to the one or more anatomical structures based on the relative positions and the defined configuration of the instrument. For example, the representations can respectively correspond to different positions, orientation, and perspectives of the instrument relative to the one or more anatomical structures over the course of surgery. At 1608, the device can display (e.g., via display component 118) the one or more representations on a first display of the device. The one or more representations can facilitate guidance of the instrument to a target location within the body.

FIG. 17 illustrates a flow diagram of another example, non-limiting method 1700 facilitating surgery using augmented reality in accordance with one or more embodiments described herein. At 1702, a device (e.g., imaging device 116) including a processor can receive image data associated with an external portion of an instrument (e.g., instrument 106) as it is inserted into a body of a patient. The image data can include at least a fiducial marker on the external portion of the instrument. At 1704, the device can determine relative positions of an internal portion of the instrument within the body relative to one or more anatomical structures of the body based on the image data and a known size and shape of the instrument.

At 1706, the device can generate representations of the instrument within the body relative to the one or more anatomical structures based on the relative positions and the known size and shape of the instrument. For example, the representations can respectively correspond to different positions, orientation, and perspectives of the instrument relative to the one or more anatomical structures over the course of surgery.

At 1708, the device can determine a trajectory of path of the instrument within the body based on the relative positions of the instrument within the body relative to the one or more anatomical structures. At 1710, the device can determine an error in a current position of the instrument within the body based on the trajectory path and a target location for the instrument within the body. At 1712, the device can determine a change to the current position of the instrument based on the error, and at 1714, the device can output information associated with an instruction regarding the change (e.g., visual and/or audible instruction) to the current position of the instrument.

Figure 18:
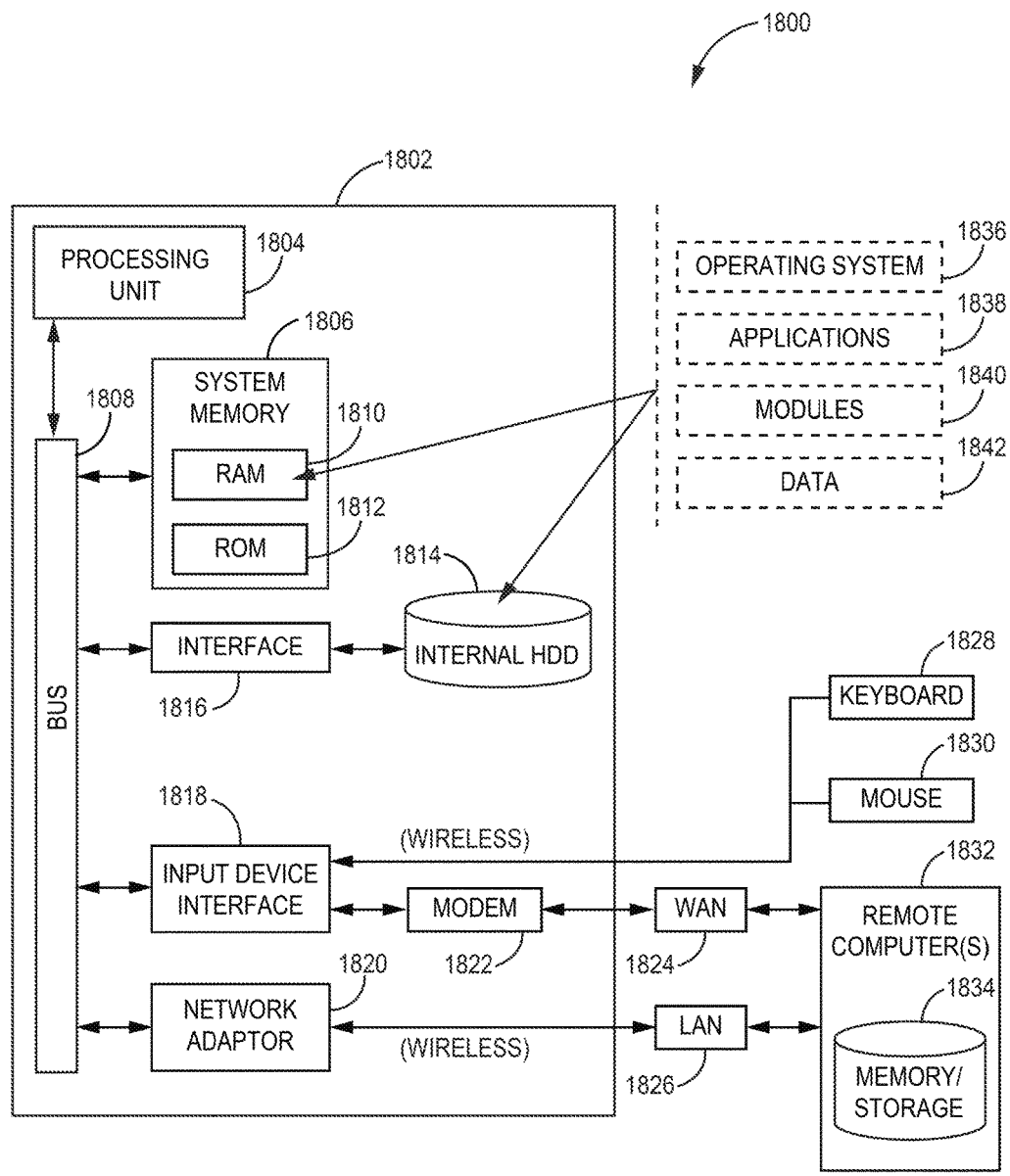
FIG. 18 illustrates a block diagram of an example, non-limiting environment including a computer operable to facilitate surgery using augmented reality in accordance with one or more embodiments described herein.

FIG. 18 illustrates a block diagram of an example, non-limiting environment including a computer operable to facilitate surgery using augmented reality in accordance with one or more embodiments described herein. FIG. 18 and the following discussion are intended to provide a brief, general description of a suitable computing environment 1800 in which the one or more embodiments described herein can be implemented. The computer 1802 can be or include the image capture device 114, imaging device 116, display component 118, orientation unit 126 and/or device 502 in accordance with one or more embodiments described herein. Repetitive description of like elements employed in other embodiments described herein is omitted for sake of brevity.

Generally, program modules include routines, programs, components, data structures, etc., that perform particular tasks or implement particular abstract data types. Moreover, those skilled in the art will appreciate that the inventive methods can be practiced with other computer system configurations, including single-processor or multiprocessor computer systems, minicomputers, mainframe computers, as well as personal computers, hand-held computing devices, microprocessor-based or programmable consumer electronics, and the like, each of which can be operatively coupled to one or more associated devices.

Computing devices typically include a variety of media, which can include computer-readable storage media and/or communications media, which two terms are used herein differently from one another as follows. Computer-readable storage media can be any available storage media that can be accessed by the computer and includes both volatile and nonvolatile media, removable and non-removable media. By way of example, and not limitation, computer-readable storage media can be implemented in connection with any method or technology for storage of information such as computer-readable instructions, program modules, structured data or unstructured data. Tangible and/or non-transitory computer-readable storage media can include, but are not limited to, random access memory (RAM), read only memory (ROM), electrically erasable programmable read only memory (EEPROM), flash memory or other memory technology, compact disk read only memory (CD-ROM), digital versatile disk (DVD) or other optical disk storage, magnetic cassettes, magnetic tape, magnetic disk storage, other magnetic storage devices and/or other media that can be used to store desired information. Computer-readable storage media can be accessed by one or more local or remote computing devices, e.g., via access requests, queries or other data retrieval protocols, for a variety of operations with respect to the information stored by the medium.

In this regard, the term "tangible" herein as applied to storage, memory, computer-readable media or computer-readable storage media, is to be understood to exclude only propagating intangible signals per se as a modifier and does not relinquish coverage of all standard storage, memory, computer-readable media or computer-readable storage media that are not only propagating intangible signals per se.

In this regard, the term "non-transitory" herein as applied to storage, memory, computer-readable media or computer-readable storage media, is to be understood to exclude only propagating transitory signals per se as a modifier and does not relinquish coverage of all standard storage, memory, computer-readable media or computer-readable storage media that are not only propagating transitory signals per se.

Communications media typically embody computer-readable instructions, data structures, program modules or other structured or unstructured data in a data signal such as a modulated data signal, e.g., a channel wave or other transport mechanism, and includes any information delivery or transport media. The term "modulated data signal" or signals refers to a signal that has one or more of the data signal's characteristics set or changed in such a manner as to encode information in one or more signals. By way of example, and not limitation, communication media include wired media, such as a wired network or direct-wired connection, and wireless media such as acoustic, RF, infrared and other wireless media.

With reference again to FIG. 18, example environment 1800 that can be employed to implement one or more embodiments of the embodiments described herein includes computer 1802. Computer 1802 includes processing unit 1804, system memory 1806 and system bus 1808. System bus 1808 couples system components including, but not limited to, system memory 1806 to processing unit 1804. Processing unit 1804 can be any of various commercially available processors. Dual microprocessors and other multi-processor architectures can also be employed as processing unit 1804.

System bus 1808 can be any of several types of bus structure that can further interconnect to a memory bus (with or without a memory controller), a peripheral bus, and a local bus using any of a variety of commercially available bus architectures. System memory 1806 includes RAM 1810 and ROM 1812. A basic input/output system (BIOS) can be stored in a non-volatile memory such as ROM, erasable programmable read only memory (EPROM), EEPROM, which BIOS contains the basic routines that help to transfer information between elements within computer 1802, such as during startup. RAM 1810 can also include a high-speed RAM such as static RAM for caching data.

Computer 1802 further includes internal hard disk drive (HDD) 1814 (e.g., Enhanced Integrated Drive Electronics (EIDE), Serial Advanced Technology Attachment (SATA)). HDD 1814 can be connected to system bus 1808 by hard disk drive interface 1816. The drives and their associated computer-readable storage media provide nonvolatile storage of data, data structures, computer-executable instructions, and so forth. For computer 1802, the drives and storage media accommodate the storage of any data in a suitable digital format.

A number of program modules can be stored in the drives and RAM 1810, including operating system 1836, one or more application programs 1838, other program modules 1840 and program data 1842. All or portions of the operating system, applications, modules, and/or data can also be cached in RAM 1810. The systems and methods described herein can be implemented utilizing various commercially available operating systems or combinations of operating systems.

A mobile device can enter commands and information into computer 1802 through one or more wireless input devices, e.g., wireless keyboard 1828 and a pointing device, such as wireless mouse 1830. Other input devices (not shown) can include a smart phone, tablet, laptop, wand, wearable device or the like. These and other input devices are often connected to the processing unit 1804 through input device interface 1818 that can be coupled to system bus 1808, but can be connected by other interfaces, such as a parallel port, an IEEE serial port, a game port and/or a universal serial bus (USB) port.

Computer 1802 can operate in a networked environment using logical connections via wired and/or wireless communications to one or more remote computers, such as remote computer(s) 1832. Remote computer(s) 1832 can be a workstation, a server computer, a router, a personal computer, portable computer, microprocessor-based entertainment appliance, a peer device or other common network node, and typically includes many or all of the elements described relative to computer 1802, although, for purposes of brevity, only memory/storage device 1834 is illustrated. The logical connections depicted include wired/wireless connectivity to a local area network (LAN) 1826 and/or larger networks, e.g., WAN 1824, as well as smaller PANs involving a few devices (e.g., at least two). LAN and WAN networking environments are commonplace in the home, offices (e.g., medical facility offices, hospital offices) and companies, and facilitate enterprise-wide computer networks, such as intranets, all of which can connect to a global communications network (e.g., the Internet).

When used in a LAN networking environment, computer 1802 can be connected to local network through a wired and/or wireless communication network interface or adapter 1820. Adapter 1820 can facilitate wired or wireless communication to LAN 1826, which can also include a wireless access point (AP) connected to the LAN 1826 for communicating with adapter 1820.

When used in a WAN networking environment, computer 1802 can include modem 1822 or can be connected to a communications server on WAN 1824 or has other means for establishing communications over WAN 1824, such as by way of the Internet. Modem 1822, which can be internal or external and a wired or wireless device, can be connected to system bus 1808 via input device interface 1816. In a networked environment, program modules depicted relative to computer 1802 or portions thereof, can be stored in a remote memory/storage device. It will be appreciated that the network connections shown are example and other means of establishing a communications link between the computers can be used.

Computer 1802 can be operable to communicate with any wireless devices or entities operatively disposed in wireless communication via any number of protocols, including, but not limited to, NFC, Wi-Fi and/or BLUETOOTH® wireless protocols. Thus, the communication can be a defined structure as with a conventional network or simply an ad hoc communication between at least two devices.

NFC can allow point-to-point connection to an NFC-enabled device in the NFC field of an IMD within the home or at any location. NFC technology can be facilitated using an NFC-enabled smart phone, tablet or other device that can be brought within 3-4 centimeters of an implanted NFC component. NFC typically provides a maximum data rate of 424 kilobits per second (Kbps), although data rates can range from 6.67 Kbps to 828 Kbps. NFC typically operates at the frequency of 13.56 megahertz (MHz). NFC technology communication is typically over a range not exceeding 0.2 meters (m) and setup time can be less than 0.1 seconds. Low power (e.g., 18 milliamperes (mAs)) reading of data can be performed by an NFC device.

Wi-Fi can allow connection to the Internet from a couch at home, a bed in a hotel room or a conference room at work, without wires. Wi-Fi is a wireless technology similar to that used in a cell phone that enables such devices, e.g., computers, to send and receive data indoors and out. Wi-Fi networks use radio technologies called IEEE 802.11 (a, b, g, n, etc.) to provide secure, reliable, fast wireless connectivity. A Wi-Fi network can be used to connect computers to each other, to the Internet, and to wired networks (which can use IEEE 802.3 or Ethernet). Wi-Fi networks operate in the unlicensed 2.4 and 5 GHz radio bands, at an 18 Mbps (802.11a) or 54 Mbps (802.11b) data rate, for example or with products that contain both bands (dual band), so the networks can provide real-world performance similar to the basic 10BaseT wired Ethernet networks used in many offices.

The embodiments of devices described herein can employ artificial intelligence (AI) to facilitate automating one or more features described herein. The embodiments (e.g., in connection with automatically identifying acquired cell sites that provide a maximum value/benefit after addition to an existing communication network) can employ various AI-based schemes for carrying out one or more embodiments thereof. Moreover, the classifier can be employed to determine a ranking or priority of each cell site of an acquired network. A classifier is a function that maps an input attribute vector, $x=(x1, x2, x3, x4, \ldots, xn)$, to a confidence that the input belongs to a class, that is, $f(x)$=confidence (class). Such classification can employ a probabilistic and/or statistical-based analysis (e.g., factoring into the analysis utilities and costs) to prognose or infer an action that a mobile device desires to be automatically performed. A support vector machine (SVM) is an example of a classifier that can be employed. The SVM operates by finding a hypersurface in the space of possible inputs, which the hypersurface attempts to split the triggering criteria from the non-triggering events. Intuitively, this makes the classification correct for testing data that is near, but not identical to training data. Other directed and undirected model classification approaches include, e.g., naïve Bayes, Bayesian networks, decision trees, neural networks, fuzzy logic models, and probabilistic classification models providing different patterns of independence can be employed. Classification as used herein also is inclusive of statistical regression that is utilized to develop models of priority.

As will be readily appreciated, one or more of the embodiments can employ classifiers that are explicitly trained (e.g., via a generic training data) as well as implicitly trained (e.g., via observing mobile device behavior, operator preferences, historical information, receiving extrinsic information). For example, SVMs can be configured via a learning or training phase within a classifier constructor and feature selection module. Thus, the classifier(s) can be used to automatically learn and perform a number of functions, including but not limited to determining according to a predetermined criteria which of the acquired cell sites will benefit a maximum number of subscribers and/or which of the acquired cell sites will add minimum value to the existing communication network coverage, etc.

As employed herein, the term "processor" can refer to substantially any computing processing unit or device including, but not limited to, single-core processors; single-processors with software multithread execution capability; multi-core processors; multi-core processors with software multithread execution capability; multi-core processors with hardware multithread technology; parallel platforms; and parallel platforms with distributed shared memory. Additionally, a processor can refer to an integrated circuit, an application specific integrated circuit (ASIC), a digital signal processor (DSP), a field programmable gate array (FPGA), a programmable logic controller (PLC), a complex programmable logic device (CPLD), a discrete gate or transistor logic, discrete hardware components or any combination thereof designed to perform the functions described herein. Processors can exploit nano-scale architectures such as, but not limited to, molecular and quantum-dot based transistors, switches and gates, in order to optimize space usage or enhance performance of mobile device equipment. A processor can also be implemented as a combination of computing processing units.

Memory disclosed herein can include volatile memory or nonvolatile memory or can include both volatile and nonvolatile memory. By way of illustration, and not limitation, nonvolatile memory can include ROM, programmable ROM (PROM), electrically programmable ROM (EPROM), electrically erasable PROM (EEPROM) or flash memory. Volatile memory can include RAM, which acts as external cache memory. By way of illustration and not limitation, RAM is available in many forms such as static RAM (SRAM), dynamic RAM (DRAM), synchronous DRAM (SDRAM), double data rate SDRAM (DDR SDRAM), enhanced SDRAM (ESDRAM), Synchlink DRAM (SLDRAM), and direct Rambus RAM (DRRAM). The memory (e.g., data storages, databases) of the embodiments is intended to include, without being limited to, these and any other suitable types of memory.

As used herein, terms such as "data storage," "database," and substantially any other information storage component relevant to operation and functionality of a component, refer to "memory components," or entities embodied in a "memory" or components including the memory. It will be appreciated that the memory components or computer-readable storage media, described herein can be either volatile memory or nonvolatile memory or can include both volatile and nonvolatile memory.

In addition, the words "example" and "exemplary" are used herein to mean serving as an instance or illustration. Any embodiment or design described herein as "example" or "exemplary" is not necessarily to be construed as preferred or advantageous over other embodiments or designs. Rather, use of the word "example" or "exemplary" is intended to present concepts in a concrete fashion. As used in this application, the term "or" is intended to mean an inclusive "or" rather than an exclusive "or". That is, unless specified otherwise or clear from context, "X employs A or B" is intended to mean any of the natural inclusive permutations. That is, if X employs A; X employs B; or X employs both A and B, then "X employs A or B" is satisfied under any of the foregoing instances. In addition, the articles "a" and "an" as used in this application should generally be construed to mean "one or more" unless specified otherwise or clear from context to be directed to a singular form. The terms "first," "second," "third," and so forth, as used in the claims and description, unless otherwise clear by context, is for clarity only and doesn't necessarily indicate or imply any order in time.

What has been described above includes mere examples of one or more embodiments. It is, of course, not possible to describe every conceivable combination of components or methodologies for purposes of describing these examples, but one of ordinary skill in the art can recognize that many further combinations and permutations of the present embodiments are possible. Accordingly, the embodiments disclosed and/or claimed herein are intended to embrace all such alterations, modifications and variations that fall within the spirit and scope of the detailed description and the appended claims. Furthermore, to the extent that the term "includes" is used in either the detailed description or the claims, such term is intended to be inclusive in a manner similar to the term "comprising" as "comprising" is interpreted when employed as a transitional word in a claim.

What is claimed is:

1. A method, comprising:
   receiving, by a first device comprising a processor, image data associated with an external portion of a tool located within a body of a patient, wherein the image data comprises first information indicative of a first fiducial marker on the external portion of the tool;
   determining one or more relative positions of an internal portion of the tool within the body relative to one or more anatomical structures of the body based on the image data and a defined configuration of the tool; and
   generating one or more representations of the tool within the body relative to the one or more anatomical structures based on the one or more relative positions and the defined configuration of the tool.

2. The method of claim 1, wherein the image data further comprises second information indicative of an external part of the body, and wherein the determining the one or more relative positions of the internal portion of the tool comprises determining one or more positions of the first fiducial marker relative to the external part of the body.

3. The method of claim 1, wherein the image data further comprises second information indicative of a second fiducial marker located on an external part of the body, and wherein the determining the one or more relative positions of the internal portion of the tool comprises determining one or more positions of the first fiducial marker relative to the second fiducial marker.

4. The method of claim 3, wherein the patient is a human and the second fiducial marker is located on an external area of the body over and adjacent to a sternum of the patient.

5. The method of claim 3, wherein the tool is inserted into the body via an incision in the body and the second fiducial marker is located proximate to the incision.

6. The method of claim 1, wherein the tool comprises an elongated shaft having a plurality of markers and the image data comprises one or more visible subsets of the plurality of markers, and wherein the determining the one or more relative positions of the internal portion of the tool within the body is based on determining the one or more visible subsets of the plurality of markers relative to the plurality of markers.

7. The method of claim 1, wherein the determining the one or more relative positions of the internal portion of the tool within the body comprises determining an orientation of the internal portion of the tool within the body.

8. The method of claim 1, wherein the tool comprises a handle and an elongated shaft and the first fiducial marker is located proximate to the handle on an outer surface of the tool.

9. The method of claim 1, further comprising:
   displaying, by the first device, the one or more representations on a first display of the first device, wherein the one or more representations facilitate guidance of the tool to a target location within the body.

10. The method of claim 1, further comprising:
    transmitting, by the first device, the one or more representations to a second device for display via a second display of the second device.

11. The method of claim 1, wherein the one or more representations are three-dimensional and the one or more anatomical structures comprise one or more internal anatomical structures of the body.

12. The method of claim 11, wherein the one or more representations comprise one or more different perspectives of the tool relative to the one or more internal anatomical structures of the body, wherein the one or more different perspectives are associated with perspectives obtained during insertion of the tool into the body.

13. The method of claim 1, further comprising:
    determining, by the first device, a trajectory path of the tool within the body based on the one or more relative positions of the tool within the body relative to the one or more anatomical structures; and identifying the trajectory path in the one or more representations.

14. The method of claim 13, further comprising:

determining, by the first device, an error in a current position of the tool within the body based on the trajectory path and a target location for the tool within the body;

determining a change to the current position of the tool based on the error; and outputting second information associated with an instruction regarding the change to the current position of the tool.

15. The method of claim 14, wherein the second information associated with the instruction comprises at least one of visual information or audible information about one or more operations to effectuate the change to the current position of the tool.

16. The method of claim 1, wherein the determining the one or more relative positions of the tool within the body comprises determining one or more distances between a distal end of the tool and a target location within the body.

17. The method of claim 1, wherein the patient is a human with a sternum and wherein the determining the one or more relative positions of the tool within the body comprises determining one or more distances between a distal end of the tool and a surface of the sternum.

18. A non-transitory computer-readable storage medium comprising computer-readable instructions that, in response to execution, cause a device to perform operations, comprising:

receiving image data associated with an external portion of a medical device inserted within a body of a patient, wherein the image data comprises first information associated with a first fiducial marker on the external portion of the medical device;

determining a relative position of an internal portion of the medical device within the body relative to one or more anatomical structures of the body based on the image data and a configuration of the medical device; and generating a representation of the internal portion of the medical device within the body relative to the one or more anatomical structures based on the relative position and the configuration of the medical device.

19. The non-transitory computer-readable storage medium of claim 18, wherein the image data further comprises second information associated with an external part of the body, and wherein the determining the relative position of the internal portion of the medical device comprises determining a position of the first fiducial marker relative to the external part of the body.

20. The non-transitory computer-readable storage medium of claim 18, wherein the first information associated with the first fiducial marker comprises a pattern, and wherein the determining the relative position of the internal portion of the medical device comprises determining an orientation of the medical device based on an appearance of the pattern in the image data.

21. The non-transitory computer-readable storage medium of claim 18, wherein the image data further comprises second information associated with a second fiducial marker located on an external part of the body, and wherein the determining the relative position of the internal portion of the medical device comprises determining a position of the first fiducial marker relative to the second fiducial marker.

22. The non-transitory computer-readable storage medium of claim 21, wherein the configuration of the medical device comprises a size and a shape of the medical device.

23. The non-transitory computer-readable storage medium of claim 18, wherein the determining the relative position of the medical device within the body comprises determining a distance between a distal end of the medical device and a surface of a sternum of the body.

* * * * *